(12) United States Patent
Lukyanov et al.

(10) Patent No.: US 7,972,834 B2
(45) Date of Patent: Jul. 5, 2011

(54) MODIFIED FLUORESCENT PROTEINS AND METHODS FOR USING SAME

(75) Inventors: Sergey A. Lukyanov, Moscow (RU); Dmitry M. Chudakov, Moscow (RU)

(73) Assignee: Evrogen IP Joint Stock Company, Moscow (RU)

( * ) Notice: Subject to any disclaimer, the term of this patent is extended or adjusted under 35 U.S.C. 154(b) by 0 days.

(21) Appl. No.: 12/803,202

(22) Filed: Jun. 21, 2010

(65) Prior Publication Data

US 2011/0003974 A1    Jan. 6, 2011

Related U.S. Application Data

(60) Provisional application No. 61/269,985, filed on Jul. 1, 2009.

(51) Int. Cl.
*C12N 1/20* (2006.01)
*C12N 15/00* (2006.01)
*C12P 21/06* (2006.01)

(52) U.S. Cl. .................. 435/252.3; 435/69.1; 435/320.1

(58) Field of Classification Search ................. 435/69.1, 435/252.3, 320.1
See application file for complete search history.

(56) References Cited

OTHER PUBLICATIONS

Shcherbo et al., Nature Methods, 4(9), 741-745, 2007.*

* cited by examiner

*Primary Examiner* — Maryam Monshipouri
(74) *Attorney, Agent, or Firm* — Patterson & Sheridan, L.L.P.

(57) ABSTRACT

Embodiments of the present invention provide nucleic acid molecules encoding improved fluorescent mutants of the Katushka fluorescent protein, variants and derivatives thereof, as well as proteins and peptides encoded by these nucleic acids. Also of interest are proteins that are substantially similar to, or derivatives, or homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising the above-referenced nucleic acid molecules are provided. The subject protein and nucleic acid compositions find use in a variety of different applications and methods, particularly for labeling of biomolecules, cells or cell organelles. Finally, kits for use in such methods and applications are provided.

12 Claims, 6 Drawing Sheets

Fig. 1

SEQUENCE LISTING

```
<160> NUMBER OF SEQ ID NOS: 26

<210> SEQ ID NO 1
<211> LENGTH: 708
<212> TYPE: DNA
<213> ORGANISM: Artificial sequence
<220> FEATURE:
<223> OTHER INFORMATION: synthetic oligonucleotide for fluorescent
      protein Katushka

<400> SEQUENCE: 1
atggtgggtg aggatagcga gctgatcacc gagaacatgc acatgaaact gtacatggag      60
ggcaccgtga acgaccacca cttcaagtgc acatccgagg gcgaaggcaa gccctacgag     120
ggcacccaga ccatgaagat caaggtggtc gagggcggcc ctctcccctt cgccttcgac     180
atcctggcta ccagcttcat gtacggcagc aaaaccttta tcaaccacac ccagggcatc     240
cccgacttct ttaagcagtc cttccctgag ggcttcacat gggagaggat caccacatac     300
gaagacgggg gcgtgctgac cgctacccag gacaccagcc tccagaacgg ctgcctcatc     360
tacaacgtca agatcaacgg ggtgaacttc ccatccaacg gccctgtgat gcagaagaaa     420
acactcggct gggaggccag caccgagatg ctgtaccccg ctgacagcgg cctgagaggc     480
```

```
catgcccaga tggccctgaa gctcgtgggc gggggctacc tgcactgctc cctcaagacc    540
acatacagat ccaagaaacc cgctaagaac ctcaagatgc ccggcttcta cttcgtggac    600
aggagactgg aaagaatcaa ggaggccgac aagagacct acgtcgagca gcacgagatg    660
gctgtggcca ggtactgcga cctgcctagc aaactggggc acagctga                708
```

<210> SEQ ID NO 2
<211> LENGTH: 235
<212> TYPE: PRT
<213> ORGANISM: Artificial sequence
<220> FEATURE:
<223> OTHER INFORMATION: synthetic polypeptide for fluorescent protein
      Katushka
<220> FEATURE:
<221> NAME/KEY: DOMAIN
<222> LOCATION: (7)..(225)
<223> OTHER INFORMATION: GFP-like domain

<400> SEQUENCE: 2

```
Met Val Gly Glu Asp Ser Glu Leu Ile Thr Glu Asn Met His Met Lys
 1               5                  10                  15

Leu Tyr Met Glu Gly Thr Val Asn Asp His His Phe Lys Cys Thr Ser
            20                  25                  30

Glu Gly Glu Gly Lys Pro Tyr Glu Gly Thr Gln Thr Met Lys Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Ile Thr Thr Tyr Glu Asp Gly Gly Val Leu Thr Ala Thr Gln Asp Thr
           100                 105                 110

Ser Leu Gln Asn Gly Cys Leu Ile Tyr Asn Val Lys Ile Asn Gly Val
       115                 120                 125

Asn Phe Pro Ser Asn Gly Pro Val Met Gln Lys Lys Thr Leu Gly Trp
   130                 135                 140

Glu Ala Ser Thr Glu Met Leu Tyr Pro Ala Asp Ser Gly Leu Arg Gly
145                 150                 155                 160

His Ala Gln Met Ala Leu Lys Leu Val Gly Gly Tyr Leu His Cys
               165                 170                 175

Ser Leu Lys Thr Thr Tyr Arg Ser Lys Lys Pro Ala Lys Asn Leu Lys
           180                 185                 190

Met Pro Gly Phe Tyr Phe Val Asp Arg Arg Leu Glu Arg Ile Lys Glu
       195                 200                 205

Ala Asp Lys Glu Thr Tyr Val Glu Gln His Glu Met Ala Val Ala Arg
   210                 215                 220

Tyr Cys Asp Leu Pro Ser Lys Leu Gly His Ser
225                 230                 235
```

<210> SEQ ID NO 3
<211> LENGTH: 735
<212> TYPE: DNA
<213> ORGANISM: Artificial sequence
<220> FEATURE:
<223> OTHER INFORMATION: synthetic oligonucleotide for fluorescent
      protein mNeptune

<400> SEQUENCE: 3

```
atggtgtcta agggcgaaga gctgattaag gagaacatgc acatgaagct gtacatggag    60
```

```
ggcaccgtga acaaccacca cttcaagtgc acatccgagg gcgaaggcaa gccctacgag    120
ggcacccaga ccggcagaat caaggtggtc gagggcggcc ctctcccctt cgccttcgac    180
atcctggcta cctgcttcat gtacggcagc aagaccttca tcaaccacac ccagggcatc    240
cccgatttct ttaagcagtc cttccctgag ggcttcacat gggagagagt caccacatac    300
gaagacgggg gcgtgctgac cgctacccag gacaccagcc tccaggacgg ctgcctcatc    360
tacaacgtca agatcagagg ggtgaacttc ccatccaacg gccctgtgat gcagaagaaa    420
acactcggct gggaggccag taccgagacg ctgtaccccg ctgacggcgg cctggaaggc    480
agatgcgaca tggccctgaa gctcgtgggc ggggccacc tgatctgcaa cctgaagacc    540
acatacagat ccaagaaacc cgctaagaac ctcaagatgc ccggcgtcta ctttgtggac    600
cgcagactgg aaagaatcaa ggaggccgac aatgagacct acgtcgagca gcacgaggtg    660
gctgtggcca gatactgcga cctccctagc aaactggggc acaaacttaa tggcatggac    720
gagctgtaca agtaa                                                     735
```

<210> SEQ ID NO 4
<211> LENGTH: 244
<212> TYPE: PRT
<213> ORGANISM: Artificial sequence
<220> FEATURE:
<223> OTHER INFORMATION: synthetic polypeptide for fluorescent protein
      mNeptune

<400> SEQUENCE: 4

```
Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Gly Arg Ile Lys
        35                  40                  45

Val Val Glu Gly Gly Pro Leu Pro Phe Ala Phe Asp Ile Leu Ala Thr
    50                  55                  60

Cys Phe Met Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Pro Ser Asn Gly Pro Val Met Gln Lys Lys Thr Leu Gly Trp
    130                 135                 140

Glu Ala Ser Thr Glu Thr Leu Tyr Pro Ala Asp Gly Gly Leu Glu Gly
145                 150                 155                 160

Arg Cys Asp Met Ala Leu Lys Leu Val Gly Gly Gly His Leu Ile Cys
                165                 170                 175

Asn Leu Lys Thr Thr Tyr Arg Ser Lys Lys Pro Ala Lys Asn Leu Lys
            180                 185                 190

Met Pro Gly Val Tyr Phe Val Asp Arg Arg Leu Glu Arg Ile Lys Glu
        195                 200                 205

Ala Asp Asn Glu Thr Tyr Val Glu Gln His Glu Val Ala Val Ala Arg
    210                 215                 220

Tyr Cys Asp Leu Pro Ser Lys Leu Gly His Lys Leu Asn Gly Met Asp
225                 230                 235                 240
```

Glu Leu Tyr Lys

<210> SEQ ID NO 5
<211> LENGTH: 699
<212> TYPE: DNA
<213> ORGANISM: Artificial sequence
<220> FEATURE:
<223> OTHER INFORMATION: synthetic oligonucleotide for fluorescent
      protein mKate2

<400> SEQUENCE: 5

```
atggtgagcg agctgattaa ggagaacatg cacatgaagc tgtacatgga gggcaccgtg      60
aacaaccacc acttcaagtg cacatccgag ggcgaaggca agccctacga gggcacccag     120
accatgagaa tcaaggcggt cgagggcggc cctctcccct cgccttcga catcctggct      180
accagcttca tgtacggcag caaaaccttc atcaaccaca cccagggcat ccccgacttc     240
tttaagcagt ccttccccga gggcttcaca tgggagagag tcaccacata cgaagacggg     300
ggcgtgctga ccgctaccca ggacaccagc ctccaggacg gctgcctcat ctacaacgtc     360
aagatcagag gggtgaactt cccatccaac ggccctgtga tgcagaagaa aacactcggc     420
tgggaggcct ccaccgagac cctgtacccc gctgacggcg gcctggaagg cagagccgac     480
atggccctga gctcgtgggc ggggggccac ctgatctgca acttgaagac acatacagga     540
tccaagaaac ccgctaagaa cctcaagatg cccggcgtct actatgtgga cagaagactg     600
gaaagaatca aggaggccga caaagagacc tacgtcgagc agcacgaggt ggctgtggcc     660
agatactgcg acctccctag caaactgggg cacagatga                            699
```

<210> SEQ ID NO 6
<211> LENGTH: 232
<212> TYPE: PRT
<213> ORGANISM: Artificial sequence
<220> FEATURE:
<223> OTHER INFORMATION: synthetic polypeptide for fluorescent protein
      mKate2
<220> FEATURE:
<221> NAME/KEY: DOMAIN
<222> LOCATION: (4)..(223)
<223> OTHER INFORMATION: GFP-like domain

<400> SEQUENCE: 6

```
Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
        115                 120                 125

Ser Asn Gly Pro Val Met Gln Lys Lys Thr Leu Gly Trp Glu Ala Ser
    130                 135                 140
```

Thr Glu Thr Leu Tyr Pro Ala Asp Gly Gly Leu Glu Gly Arg Ala Asp
145                 150                 155                 160

Met Ala Leu Lys Leu Val Gly Gly Gly His Leu Ile Cys Asn Leu Lys
            165                 170                 175

Thr Thr Tyr Arg Ser Lys Lys Pro Ala Lys Asn Leu Lys Met Pro Gly
        180                 185                 190

Val Tyr Tyr Val Asp Arg Arg Leu Glu Arg Ile Lys Glu Ala Asp Lys
    195                 200                 205

Glu Thr Tyr Val Glu Gln His Glu Val Ala Val Ala Arg Tyr Cys Asp
    210                 215                 220

Leu Pro Ser Lys Leu Gly His Arg
225                 230

<210> SEQ ID NO 7
<211> LENGTH: 705
<212> TYPE: DNA
<213> ORGANISM: Artificial sequence
<220> FEATURE:
<223> OTHER INFORMATION: synthetic oligonucleotide for fluorescent
      protein Katushka 9-5

<400> SEQUENCE: 7
atgggagagg atagcgagct gatctccgag aacatgcaca tgaaactgta catggagggc      60
accgtgaacg accaccactt caagtgcaca tccgagggcg aaggcaagcc ctacgagggc     120
acccagacca tgaagatcaa ggtggtcgag ggcggccctc tccccttcgc cttcgacatc     180
ctggctacca gcttcatgta cggcagcaaa acctttatca accacaccca gggcatcccc     240
gacttcttta agcagtcctt ccctgagggc ttcacatggg agaggatcac cacatacgaa     300
gacgggggcg tgctgaccgc tacccaggac accagcctcc agaacggctg cctcatctac     360
aacgtcaaga tcaacggggt gaacttccca tccaacggcc ctgtgatgca agagaaaaca     420
ctcggctggg aggccagcac cgagatgctg taccccgctg cagcggcct gagaggccat     480
agccagatgg ccctgaagct cgtgggcggg ggctacctgc actgctccct caagaccaca     540
tacagatcca gaaacccgc taagaacctc aagatgcccg gcttctactt cgtggacagg     600
aaactggaaa gaatcaagga ggccgacaaa gagacctacg tcgagcagca cgagatggct     660
gtggccaggt actgcgacct gcctagcaaa ctggggcaca gctga                     705

<210> SEQ ID NO 8
<211> LENGTH: 234
<212> TYPE: PRT
<213> ORGANISM: Artificial sequence
<220> FEATURE:
<223> OTHER INFORMATION: synthetic polypeptide for fluorescent protein
      Katushka 9-5

<400> SEQUENCE: 8

Met Gly Glu Asp Ser Glu Leu Ile Ser Glu Asn Met His Met Lys Leu
1               5                   10                  15

Tyr Met Glu Gly Thr Val Asn Asp His His Phe Lys Cys Thr Ser Glu
            20                  25                  30

Gly Glu Gly Lys Pro Tyr Glu Gly Thr Gln Thr Met Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Ile 85                  90                  95
Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
            115                 120                 125

Phe Pro Ser Asn Gly Pro Val Met Gln Lys Lys Thr Leu Gly Trp Glu
            130                 135                 140

Ala Ser Thr Glu Met Leu Tyr Pro Ala Asp Ser Gly Leu Arg Gly His
145                 150                 155                 160

Ser Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe Tyr Phe Val Asp Arg Lys Leu Glu Arg Ile Lys Glu Ala
            195                 200                 205

Asp Lys Glu Thr Tyr Val Glu Gln His Glu Met Ala Val Ala Arg Tyr
210                 215                 220

Cys Asp Leu Pro Ser Lys Leu Gly His Ser
225                 230

<210> SEQ ID NO 9
<211> LENGTH: 705
<212> TYPE: DNA
<213> ORGANISM: Artificial sequence
<220> FEATURE:
<223> OTHER INFORMATION: synthetic oligonucleotide for fluorescent
      protein Kat650-21

<400> SEQUENCE: 9
atgggagagg atagcgagct gatctccgag aacatgcaca tgaaactgta catggagggc      60
accgtgaacg gccaccactt caagtgcaca tccgagggcg aaggcaagcc ctacgagggc     120
acccagaccg ctaagatcaa ggtggtcgag ggcggccctc tccccttcgc cttcgacatc     180
ctggctacca gcttcatgta cggcagcaaa accttatca accacaccca gggcatcccc     240
gacttcttta gcagtccttc ccctgagggc ttcacatggg agaggatcac acatacgaa      300 gacggggcg tgctgaccgc tacccaggac accagcctcc agaacggctg cctcatctac      360
aacgtcaaga tcaacggggt gaacttccca tccaacggcc ctgtgatgca agaaaaaca      420 ctcggctggg aggccagcac cgagatgctg taccccgctg acagcggcct gagaggccat      480
agccagatgg ccctgaagct cgtgggcggg ggctacctgc actgctccct caagaccaca     540
tacagatcca agaaacccgc taagaacctc aagatgcccg gcttctactt cgtggacagg     600
aaactggaaa gaatcaagga ggccgacaaa gagacctacg tcgagcagca cgagatggct     660
gtggccaggt actgcgacct gcctagcaaa ctggggcaca gctga                    705

<210> SEQ ID NO 10
<211> LENGTH: 234
<212> TYPE: PRT
<213> ORGANISM: Artificial sequence
<220> FEATURE:
<223> OTHER INFORMATION: synthetic polypeptide for fluorescent protein
      Kat650-21
<220> FEATURE:
<221> NAME/KEY: DOMAIN
<222> LOCATION: (6)..(225)
<223> OTHER INFORMATION: GFP-like domain

<400> SEQUENCE: 10

Met Gly Glu Asp Ser Glu Leu Ile Ser Glu Asn Met His Met Lys Leu

```
                1               5                   10                  15
Tyr Met Glu Gly Thr Val Asn Gly His His Phe Lys Cys Thr Ser Glu
                    20                  25                  30
Gly Glu Gly Lys Pro Tyr Glu Gly Thr Gln Thr Ala Lys Ile Lys Val
                    35                  40                  45
Val Glu Gly Gly Pro Leu Pro Phe Ala Phe Asp Ile Leu Ala Thr Ser
                    50                  55                  60
Phe Met Tyr Gly Ser Lys Thr Phe Ile Asn His Thr Gln Gly Ile Pro
65                  70                  75                  80
Asp Phe Phe Lys Gln Ser Phe Pro Glu Gly Phe Thr Trp Glu Arg Ile
                    85                  90                  95
Thr Thr Tyr Glu Asp Gly Gly Val Leu Thr Ala Thr Gln Asp Thr Ser
                    100                 105                 110
Leu Gln Asn Gly Cys Leu Ile Tyr Asn Val Lys Ile Asn Gly Val Asn
                    115                 120                 125
Phe Pro Ser Asn Gly Pro Val Met Gln Lys Lys Thr Leu Gly Trp Glu
                    130                 135                 140
Ala Ser Thr Glu Met Leu Tyr Pro Ala Asp Ser Gly Leu Arg Gly His
145                 150                 155                 160
Ser Gln Met Ala Leu Lys Leu Val Gly Gly Gly Tyr Leu His Cys Ser
                    165                 170                 175
Leu Lys Thr Thr Tyr Arg Ser Lys Lys Pro Ala Lys Asn Leu Lys Met
                    180                 185                 190
Pro Gly Phe Tyr Phe Val Asp Arg Lys Leu Glu Arg Ile Lys Glu Ala
                    195                 200                 205
Asp Lys Glu Thr Tyr Val Glu Gln His Glu Met Ala Val Ala Arg Tyr
                    210                 215                 220
Cys Asp Leu Pro Ser Lys Leu Gly His Ser
225                 230
```

<210> SEQ ID NO 11
<211> LENGTH: 705
<212> TYPE: DNA
<213> ORGANISM: Artificial sequence
<220> FEATURE:
<223> OTHER INFORMATION: synthetic oligonucleotide for fluorescent protein Kat670-23

<400> SEQUENCE: 11

```
atgggagagg atagcgagct gatctccgag aacatgcaca cgaaactgta catggagggc      60
accgtgaacg gccaccactt caagtgcaca tccgagggcg aaggcaagcc ctacgagggc     120
acccagacct gtaagatcaa ggtggtcgag ggcggccctc tccccttcgc cttcgacatc     180
ctggctacca gcttcatgta cggcagcaaa acctttatca accacaccca gggcatcccc     240
gacttcttta gcagtccctt ccctgagggc ttcacatggg agaggatcac cacatacgaa     300
gacggggcg tgctgaccgc ctacccagga ccagcctcc agaacggctg cctcatctac       360
aacgtcaaga tcaacggggt gaacttccca tccaacggcc ctgtgatgca agaaaaaca      420
ctcggctggg aggccaacac cgagatgctg taccccgctg acagcggtct gagaggccat     480
aatcagatgg ccctgaagct cgtgggcggg ggctacctgc actgctccct caagaccaca     540
tacagatcca agaaacccgc taagaacctc aagatgcccg gcttctactt cgtggaccgt     600
aaactggaaa gaatcaagga ggccgacaaa gagacctacg tcgagcagca cgagatggct     660
gtggccaggt actgcgacct gcctagcaaa ctggggcaca gctga                     705
```

<210> SEQ ID NO 12
<211> LENGTH: 234
<212> TYPE: PRT
<213> ORGANISM: Artificial sequence
<220> FEATURE:
<223> OTHER INFORMATION: synthetic polypeptide for fluorescent protein Kat670-23
<220> FEATURE:
<221> NAME/KEY: DOMAIN
<222> LOCATION: (6)..(225)
<223> OTHER INFORMATION: GFP-like domain

<400> SEQUENCE: 12

```
Met Gly Glu Asp Ser Glu Leu Ile Ser Glu Asn Met His Thr Lys Leu
1               5                   10                  15

Tyr Met Glu Gly Thr Val Asn Gly His His Phe Lys Cys Thr Ser Glu
            20                  25                  30

Gly Glu Gly Lys Pro Tyr Glu Gly Thr Gln Thr Cys Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
        115                 120                 125

Phe Pro Ser Asn Gly Pro Val Met Gln Lys Lys Thr Leu Gly Trp Glu
    130                 135                 140

Ala Asn Thr Glu Met Leu Tyr Pro Ala Asp Ser Gly Leu Arg Gly His
145                 150                 155                 160

Asn Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe Tyr Phe Val Asp Arg Lys Leu Glu Arg Ile Lys Glu Ala
        195                 200                 205

Asp Lys Glu Thr Tyr Val Glu Gln His Glu Met Ala Val Ala Arg Tyr
    210                 215                 220

Cys Asp Leu Pro Ser Lys Leu Gly His Ser
225                 230
```

<210> SEQ ID NO 13
<211> LENGTH: 705
<212> TYPE: DNA
<213> ORGANISM: Artificial sequence
<220> FEATURE:
<223> OTHER INFORMATION: synthetic oligonucleotide for fluorescent protein KatX1

<400> SEQUENCE: 13

```
atgggagagg atagcgagct gatctccgag aacatgcaca cgaaagagta catggagggc    60
accgtgaacg gccaccactt caagtgcaca tccagggcg aaggcaagcc ctacgagggc   120
acccagacct gtaagatcaa ggtggtcgag ggcggccctc tccccttcgc cttcgacatc   180
ctggctacca gcttcatgta cggcagcaaa acctttatca accacaccca gggcatcccc   240
gacttcttta agcagtcctt ccctgagggc ttcacatggg agaggatcac cacatacgaa   300
```

-continued

```
gacgggggcg tgctgaccgc tacccaggac accagcctcc agaacggctg cctcatctac    360
aacgtcaaga tcaacggggt gaacttccca tccaacggcc tgtgatgca agaaaaaca     420 ctcggctggg aggccaacac cgagatgctg taccccgctg acagcggtct gagaggccat    480
aatcagatgg ccctgaagct cgtgggcggg ggctacctgc actgctccct caagaccaca   540
tacagatcca agaaacccgc taagaacctc aagatgcccg gcttctactt cgtggaccgt    600
aaactggaaa gaatcaagga ggccgacaaa gagacctacg tcgagcagca cgagatggct    660
gtggccaggt actgcgacct gcctagcaaa ctggggcaca gctga                    705
```

<210> SEQ ID NO 14
<211> LENGTH: 234
<212> TYPE: PRT
<213> ORGANISM: Artificial sequence
<220> FEATURE:
<223> OTHER INFORMATION: synthetic polypeptide for fluorescent protein KatX1

<400> SEQUENCE: 14

```
Met Gly Glu Asp Ser Glu Leu Ile Ser Glu Asn Met His Thr Lys Glu
1               5                   10                  15
Tyr Met Glu Gly Thr Val Asn Gly His His Phe Lys Cys Thr Ser Glu
            20                  25                  30
Gly Glu Gly Lys Pro Tyr Glu Gly Thr Gln Thr Cys Lys Ile Lys Val
        35                  40                  45
Val Glu Gly Gly Pro Leu Pro Phe Ala Phe Asp Ile Leu Ala Thr Ser
    50                  55                  60
Phe Met Tyr Gly Ser Lys Thr Phe Ile Asn His Thr Gln Gly Ile Pro
65                  70                  75                  80
Asp Phe Phe Lys Gln Ser Phe Pro Glu Gly Phe Thr Trp Glu Arg Ile
                85                  90                  95
Thr Thr Tyr Glu Asp Gly Gly Val Leu Thr Ala Thr Gln Asp Thr Ser
            100                 105                 110
Leu Gln Asn Gly Cys Leu Ile Tyr Asn Val Lys Ile Asn Gly Val Asn
        115                 120                 125
Phe Pro Ser Asn Gly Pro Val Met Gln Lys Lys Thr Leu Gly Trp Glu
    130                 135                 140
Ala Asn Thr Glu Met Leu Tyr Pro Ala Asp Ser Gly Leu Arg Gly His
145                 150                 155                 160
Asn Gln Met Ala Leu Lys Leu Val Gly Gly Gly Tyr Leu His Cys Ser
                165                 170                 175
Leu Lys Thr Thr Tyr Arg Ser Lys Lys Pro Ala Lys Asn Leu Lys Met
            180                 185                 190
Pro Gly Phe Tyr Phe Val Asp Arg Lys Leu Glu Arg Ile Lys Glu Ala
        195                 200                 205
Asp Lys Glu Thr Tyr Val Glu Gln His Glu Met Ala Val Ala Arg Tyr
    210                 215                 220
Cys Asp Leu Pro Ser Lys Leu Gly His Ser
225                 230
```

<210> SEQ ID NO 15
<211> LENGTH: 705
<212> TYPE: DNA
<213> ORGANISM: Artificial sequence
<220> FEATURE:
<223> OTHER INFORMATION: synthetic oligonucleotide for fluorescent protein KatX2

<400> SEQUENCE: 15

```
atgggagagg atagcgagct gatctccgag aacatgcaca cgaaagagta catggagggc    60
accgtgaacg gccaccactt caagtgcaca tccgagggcg aaggcaagcc ctacgagggc   120
acccagaccg ctaagatcaa ggtggtcgag ggcggccctc tccccttcgc cttcgacatc   180
ctggctacca gcttcatgta cggcagcaaa acctttatca accacaccca gggcatcccc   240
gacttcttta gcagtccctt ccctgagggc ttcacatggg agaggatcac acatacgaa    300 gacggggcg tgctgaccgc tacccaggac accagcctcc agaacggctg cctcatctac   360
aacgtcaaga tcaacggggt gaacttccca tccaacggcc tgtgatgca aagaaaaca    420 ctcggctggg aggccagcac cgagatgctg taccccgctg acagcggcct gagaggccat   480
agccagatgg ccctgaagct cgtgggcggg ggctacctgc actgctccct caagaccaca   540
tacagatcca agaaacccgc taagaacctc aagatgcccg cttctactt cgtggacagg   600 aaactggaaa gaatcaagga ggccgacaaa gagacctacg tcgagcagca cgagatggct   660
gtggccaggt actgcgacct gcctagcaaa ctggggcaca gctga             705
```

<210> SEQ ID NO 16
<211> LENGTH: 234
<212> TYPE: PRT
<213> ORGANISM: Artificial sequence
<220> FEATURE:
<223> OTHER INFORMATION: synthetic polypeptide for fluorescent protein KatX2

<400> SEQUENCE: 16

```
Met Gly Glu Asp Ser Glu Leu Ile Ser Glu Asn Met His Ser Lys Glu
1               5                   10                  15

Tyr Met Glu Gly Thr Val Asn Gly His His Phe Lys Cys Thr Ser Glu
            20                  25                  30

Gly Glu Gly Lys Pro Tyr Glu Gly Thr Gln Thr Ala Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
        115                 120                 125

Phe Pro Ser Asn Gly Pro Val Met Gln Lys Lys Thr Leu Gly Trp Glu
    130                 135                 140

Ala Ser Thr Glu Met Leu Tyr Pro Ala Asp Ser Gly Leu Arg Gly His
145                 150                 155                 160

Ser Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe Tyr Phe Val Asp Arg Lys Leu Glu Arg Ile Lys Glu Ala
        195                 200                 205

Asp Lys Glu Thr Tyr Val Glu Gln His Glu Met Ala Val Ala Arg Tyr
    210                 215                 220

Cys Asp Leu Pro Ser Lys Leu Gly His Ser
225                 230
```

<210> SEQ ID NO 17
<211> LENGTH: 702
<212> TYPE: DNA
<213> ORGANISM: Artificial sequence
<220> FEATURE:
<223> OTHER INFORMATION: synthetic oligonucleotide for fluorescent protein Katushka 9-5A

<400> SEQUENCE: 17

```
atgggagagg atagcgagct gatctccgag aacatgcaca tgaaactgta catggagggc      60
accgtgaacg accaccactt caagtgcaca tccgagggcg aaggcaagcc ctacgagggc     120
acccagacca tgaagatcaa ggtggtcgag ggcggccctc tccccttcgc cttcgacatc     180
ctggctacca gcttcatgta cggcagcaaa acctttatca accacaccca gggcatcccc     240
gacttcttta gcagtccttc cctgagggc ttcacatggg agaggatcac cacatacgaa      300
gacgggggcg tgctgaccgc tacccaggac accagcctcc agaacggctg cctcatctac     360
aacgtcaaga tcaacggggt gaacttccca tccaacggcc ctgtgatgca agaaaaaca      420
ctcggctggg aggccagcac cgagatgctg taccccgctg acagcggcct gagaggccat     480
gcccagatgg ccctgaagct cgtgggcggg ggctacctgc actgctccct caagaccaca     540
tacagatcca agaaacccgc taagaacctc aagatgcccg cttctactt cgtggacagg      600
aaactggaaa gaatcaagga ggccgacaaa gagacctacg tcgagcagca cgagatggct     660
gtggccaggt actgcgacct gcctagcaaa ctggggcaca gc                        702
```

<210> SEQ ID NO 18
<211> LENGTH: 234
<212> TYPE: PRT
<213> ORGANISM: Artificial sequence
<220> FEATURE:
<223> OTHER INFORMATION: synthetic polypeptide for fluorescent protein Katushka 9-5A

<400> SEQUENCE: 18

```
Met Gly Glu Asp Ser Glu Leu Ile Ser Glu Asn Met His Met Lys Leu
1               5                   10                  15

Tyr Met Glu Gly Thr Val Asn Asp His His Phe Lys Cys Thr Ser Glu
            20                  25                  30

Gly Glu Gly Lys Pro Tyr Glu Gly Thr Gln Thr Met Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
        115                 120                 125

Phe Pro Ser Asn Gly Pro Val Met Gln Lys Lys Thr Leu Gly Trp Glu
    130                 135                 140

Ala Ser Thr Glu Met Leu Tyr Pro Ala Asp Ser Gly Leu Arg Gly His
145                 150                 155                 160

Ala Gln Met Ala Leu Lys Leu Val Gly Gly Gly Tyr Leu His Cys Ser
                165                 170                 175
```

```
Leu Lys Thr Thr Tyr Arg Ser Lys Lys Pro Ala Lys Asn Leu Lys Met
            180                 185                 190

Pro Gly Phe Tyr Phe Val Asp Arg Lys Leu Glu Arg Ile Lys Glu Ala
        195                 200                 205

Asp Lys Glu Thr Tyr Val Glu Gln His Glu Met Ala Val Ala Arg Tyr
    210                 215                 220

Cys Asp Leu Pro Ser Lys Leu Gly His Ser
225                 230
```

<210> SEQ ID NO 19
<211> LENGTH: 705
<212> TYPE: DNA
<213> ORGANISM: Artificial sequence
<220> FEATURE:
<223> OTHER INFORMATION: synthetic oligonucleotide for fluorescent
      protein Kat683-1

<400> SEQUENCE: 19

```
atgggagagg atagcgagct gatctccgag aacatgcaca cgaaaaacta catggagggc      60
accgtgaacg gccaccactt caagtgcaca tccgagggcg aaggcaagcc ctacgagggc     120
acccagacct gtaagatcaa ggtggtcgag ggcggccctc tccccttcgc cttcgacatc     180
ctggctacca gcttcatgta cggcagcaaa acctttatca accacaccca gggcatcccc     240
gacttcttta gcagtccttc cctgagggc ttcacatggg agaggatcac cacatacgaa      300
gacgggggcg tgctgaccgc tacccaggac accagcctcc agaacggctg cctcatctac     360
aacgtcaaga tcaacggggt gaacttccca tccaacggcc ctgtgatgca gaagaaaaca     420
ctcggctggg aggccaacac cgagatgctg taccccgctg acagcggtct gagaggccat     480
aatcagatgg ccctgaagct cgtgggcggg ggctacctgc actgctccct caagaccaca     540
tacagatcca gaaacccgc taagaacctc aagatgcccg gcttctactt cgtggaccgt     600
aaactggaaa gaatcaagga ggccgacaaa gagacctacg tcgagcagca cgagatggct     660
gtggccaggt actgcgacct gcctagcaaa ctggggcaca gctga                    705
```

<210> SEQ ID NO 20
<211> LENGTH: 234
<212> TYPE: PRT
<213> ORGANISM: Artificial sequence
<220> FEATURE:
<223> OTHER INFORMATION: synthetic polypeptide for fluorescent protein
      Kat683-1

<400> SEQUENCE: 20

```
Met Gly Glu Asp Ser Glu Leu Ile Ser Glu Asn Met His Thr Lys Asn
1               5                   10                  15

Tyr Met Glu Gly Thr Val Asn Gly His His Phe Lys Cys Thr Ser Glu
            20                  25                  30

Gly Glu Gly Lys Pro Tyr Glu Gly Thr Gln Thr Cys Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
```

```
                115                 120                 125
Phe Pro Ser Asn Gly Pro Val Met Gln Lys Lys Thr Leu Gly Trp Glu
    130                 135                 140

Ala Asn Thr Glu Met Leu Tyr Pro Ala Asp Ser Gly Leu Arg Gly His
145                 150                 155                 160

Asn Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe Tyr Phe Val Asp Arg Lys Leu Glu Arg Ile Lys Glu Ala
        195                 200                 205

Asp Lys Glu Thr Tyr Val Glu Gln His Glu Met Ala Val Ala Arg Tyr
    210                 215                 220

Cys Asp Leu Pro Ser Lys Leu Gly His Ser
225                 230

<210> SEQ ID NO 21
<211> LENGTH: 226
<212> TYPE: PRT
<213> ORGANISM: Artificial sequence
<220> FEATURE:
<223> OTHER INFORMATION: synthetic polypeptide for fluorescent protein
      mPlum

<400> SEQUENCE: 21

Met Val Ser Lys Gly Glu Glu Val Ile Lys Glu Phe Met Arg Phe Lys
1               5                   10                  15

Glu His Met Glu Gly Ser Val Asn Gly His Glu Phe Glu Ile Glu Gly
                20                  25                  30

Glu Gly Glu Gly Arg Pro Tyr Glu Gly Thr Gln Thr Ala Arg Leu Lys
            35                  40                  45

Val Thr Lys Gly Gly Pro Leu Pro Phe Ala Trp Asp Ile Leu Ser Pro
    50                  55                  60

Gln Ile Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Val Arg Gly Thr
        115                 120                 125

Asn Phe Pro Ser Asp Gly Pro Val Met Gln Lys Lys Thr Met Gly Trp
    130                 135                 140

Glu Ala Ser Ser Glu Arg Met Tyr Pro Glu Asp Gly Ala Leu Lys Gly
145                 150                 155                 160

Glu Met Lys Met Arg Leu Arg Leu Lys Asp Gly Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225
```

-continued

<210> SEQ ID NO 22
<211> LENGTH: 226
<212> TYPE: PRT
<213> ORGANISM: Artificial sequence
<220> FEATURE:
<223> OTHER INFORMATION: synthetic polypeptide for fluorescent protein
      mRaspberry

<400> SEQUENCE: 22

Met Val Ser Lys Gly Glu Glu Val Ile Lys Glu Phe Met Arg Phe Lys
1               5                   10                  15

Val Arg Met Glu Gly Ser Val Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Cys Met Tyr Gly Ser Lys Gly Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Leu Arg Gly Thr
        115                 120                 125

Asn Phe Pro Ser Asp Gly Pro Val Met Gln Lys Lys Thr Met Gly Trp
    130                 135                 140

Glu Ala Ser Ser Glu Arg Met Tyr Pro Glu Asp Gly Ala Leu Lys Gly
145                 150                 155                 160

Glu Met Lys Met Arg Leu Lys Leu Lys Asp Gly Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225

<210> SEQ ID NO 23
<211> LENGTH: 231
<212> TYPE: PRT
<213> ORGANISM: Artificial sequence
<220> FEATURE:
<223> OTHER INFORMATION: synthetic polypeptide for fluorescent protein
      FP611

<400> SEQUENCE: 23

Met Asn Ser Leu Ile Lys Glu Asn Met Arg Met Met Val Val Met Glu
1               5                   10                  15

Gly Ser Val Asn Gly Tyr Gln Phe Lys Cys Thr Gly Glu Gly Asp Gly
            20                  25                  30

Asn Pro Tyr Met Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Lys Thr Phe Ile Lys His Thr Lys Gly Ile Pro Asp Phe Phe
65                  70                  75                  80

```
Lys Gln Ser Phe Pro Glu Gly Phe Thr Trp Glu Arg Val Thr Arg Tyr
                85                  90                  95

Glu Asp Gly Gly Val Phe Thr Val Met Gln Asp Thr Ser Leu Glu Asp
            100                 105                 110

Gly Cys Leu Val Tyr His Ala Lys Val Thr Gly Val Asn Phe Pro Ser
        115                 120                 125

Asn Gly Ala Val Met Gln Lys Lys Thr Lys Gly Trp Glu Pro Asn Thr
130                 135                 140

Glu Met Leu Tyr Pro Ala Asp Gly Gly Leu Arg Gly Tyr Ser Gln Met
145                 150                 155                 160

Ala Leu Asn Val Asp Gly Gly Tyr Leu Ser Cys Ser Phe Glu Thr
                165                 170                 175

Thr Tyr Arg Ser Lys Lys Thr Val Glu Asn Phe Lys Met Pro Gly Phe
            180                 185                 190

His Phe Val Asp His Arg Leu Glu Arg Leu Glu Glu Ser Asp Lys Glu
        195                 200                 205

Met Phe Val Val Gln His Glu His Ala Val Ala Lys Phe Cys Asp Leu
210                 215                 220

Pro Ser Lys Leu Gly Arg Leu
225                 230

<210> SEQ ID NO 24
<211> LENGTH: 238
<212> TYPE: PRT
<213> ORGANISM: Aequorea victoria
<220> FEATURE:
<221> NAME/KEY: DOMAIN
<222> LOCATION: (6)..(229)
<220> FEATURE:
<221> NAME/KEY: DOMAIN
<222> LOCATION: (6)..(229)
<223> OTHER INFORMATION: GFP-like domain

<400> SEQUENCE: 24

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
```

```
                  180                 185                 190
Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235

<210> SEQ ID NO 25
<211> LENGTH: 678
<212> TYPE: DNA
<213> ORGANISM: Artificial sequence
<220> FEATURE:
<223> OTHER INFORMATION: synthetic oligonucleotide for fluorescent
      protein E2-Crimson

<400> SEQUENCE: 25
atggatagca ctgagaacgt catcaagccc ttcatgcgct tcaaggtgca catggagggc      60
tccgtgaacg gccacgagtt cgagatcgag ggcgtgggcg agggcaagcc ctacgagggc     120
acccagaccg ccaagctgca agtgaccaag ggcggccccc tgcccttcgc ctgggacatc     180 ctgtccccc  agttcttcta cggctccaag gcgtacatca agcaccccgc cgacatcccc     240
gactacctca gcagtccttc ccccgagggc ttcaagtggg agcgcgtgat gaacttcgag     300
gacggcggcg tggtgaccgt gacccaggac tcctccctgc aggacggcac cctcatctac     360
cacgtgaagt tcatcggcgt gaacttcccc tccgacggcc ccgtaatgca gaagaagact     420
ctgggctggg agccctccac tgagcgcaac taccccgcg  acgccgtgct gaagggcgag     480
aaccacatgg cgctgaagct gaagggcggc ggccactacc tgtgtgagtt caagtccatc     540
tacatggcca agaagcccgt gaagctgccc ggctaccact acgtggacta caagctcgac     600
atcacctccc acaacgagga ctacaccgtg gtggagcagt acgagcgcgc cgaggcccgc     660
caccacctgt tccagtag                                                   678

<210> SEQ ID NO 26
<211> LENGTH: 225
<212> TYPE: PRT
<213> ORGANISM: Artificial sequence
<220> FEATURE:
<223> OTHER INFORMATION: synthetic polypeptide for fluorescent protein
      E2-Crimson

<400> SEQUENCE: 26

Met Asp Ser Thr Glu Asn Val Ile Lys Pro Phe Met Arg Phe Lys Val
1               5                   10                  15

His Met Glu Gly Ser Val Asn Gly His Glu Phe Glu Ile Glu Gly Val
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Phe Tyr Gly Ser Lys Ala Tyr Ile Lys His Pro Ala Asp Ile Pro
65                  70                  75                  80

Asp Tyr Leu Lys Gln Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Thr Leu Ile Tyr His Val Lys Phe Ile Gly Val Asn
        115                 120                 125
```

```
Phe Pro Ser Asp Gly Pro Val Met Gln Lys Lys Thr Leu Gly Trp Glu
        130             135             140
Pro Ser Thr Glu Arg Asn Tyr Pro Arg Asp Gly Val Leu Lys Gly Glu
145             150             155             160
Asn His Met Ala Leu Lys Leu Lys Gly Gly Gly His Tyr Leu Cys Glu
            165             170                 175
Phe Lys Ser Ile Tyr Met Ala Lys Lys Pro Val Lys Leu Pro Gly Tyr
            180             185             190
His Tyr Val Asp Tyr Lys Leu Asp Ile Thr Ser His Asn Glu Asp Tyr
        195             200             205
Thr Val Val Glu Gln Tyr Glu Arg Ala Glu Ala Arg His His Leu Phe
        210             215             220
Gln
225
```

MODIFIED FLUORESCENT PROTEINS AND METHODS FOR USING SAME

CROSS-REFERENCE TO RELATED APPLICATIONS

This application claims benefit of U.S. provisional patent application Ser. No. 61/269,985, filed Jul. 1, 2009, which is herein incorporated by reference in its entirety.

BACKGROUND OF THE INVENTION

1. Field of the Invention

Fluorescent proteins and nucleic acids that encode fluorescent proteins are provided. Also provided are methods for their use, and reagents, devices and kits for use in these methods.

2. Description of the Related Art

Labeling of a protein, cell, or organism of interest plays a prominent role in many biochemical, molecular biological, and medical diagnostic applications. A variety of different labels have been developed and used in the art, including radiolabels, chromolabels, fluorescent labels, chemilluminescent labels, and the like, with varying properties and optimal uses. However, there is continued interest in the development of new labels. Of particular interest is the development of new protein labels, including fluorescent protein labels.

Green Fluorescent Protein (GFP) from the hydromedusa *Aequorea aequorea/Aequorea victoria* (*A. victoria*) was identified by Johnson et al., J. Cell Comp. Physiol. (1962) 60:85-104 as a secondary emitter of the jellyfish's bioluminescent system, transforming blue light from the photoprotein aequorin into green light. The cDNA encoding *A. victoria* GFP (avGFP) was cloned as reported in Prasher et al., Gene (1992) 111:229-33 (SEQ ID NO:24). When ectopically expressed, this gene will produce a fluorescent protein due to its unique ability to independently form a chromophore (Chalfie et al., Gene (1992) 111:229-233). This finding has enabled broad applications for the use of GFP in cell biology as a genetically encoded fluorescent label.

Genes encoding fluorescent proteins have since been cloned from organisms of a wide variety of different phylogenetic clades including, but not limited to: Hydrozoa, Anthozoa, Arthropoda (Copepoda) and Chordrata (Brachiostoma), e.g., as reported in: Matz et al., Nat. Biotechnol. (1999) 17: 969-973; Chudakov et al., Trends Biotechnol. (2005) 23: 605-613; Shagin et al., Mol. Biol. Evol. (2004) 21: 841-850; Masuda et al., Gene (2006) 372: 18-25; Deheyn et al., Biol. Bull. (2007) 213: 95-100; and Baumann et al., Biol. Direct. (2008) 3: 28. Currently, the fluorescent protein (FP) family (also referred to in the art as the "GFP family") includes hundreds of member proteins. While these proteins may collectively be referred to as members of the "GFP family", emission maxima may vary widely in terms of wavelength, and therefore not all members of the family fluoresce green.

Proteins of the GFP family share a common GFP-like domain. This domain can be easily identified in the amino acid sequences of the various family members using available software for the analysis of protein domain organization, e.g., by using the Conserved Domain Database (CDD) program available at the website formed by placed "http://www." in front of "ncbi.nlm.nih.gov/Structure/cdd/" and the Simple Modular Architecture Research Tool (SMART) program available at the website formed by placing "http://smart." in front of "embl-heidelberg.de/". For example, the GFP-like domain of avGFP begins at amino acid residue 6 and ends at amino acid residue 229. It has been demonstrated that a core domain within this domain, the "minimum GFP-like domain," produced by truncating the protein at the N-terminus (up to 9 amino acid residues) and C-terminus (up to 11 amino acid residues) is sufficient to provide for maturation and fluorescence of GFP family proteins (Shimozono et al., Biochemistry. 2006; 45(20): 6267-71). Thus, when expressed, both GFP-like domain polypeptides and minimum GFP-like domain polypeptides can produce a protein that exhibits fluorescence.

The GFP-like domain comprises a chromophore that is responsible for the fluorescence emitted by fluorescent proteins upon irradiation with excitation light at an appropriate wavelength. The chromophore is formed by amino acids corresponding to the Ser65-Tyr66-Gly67 region of avGFP. Corresponding amino acids in fluorescent proteins other than avGFP can be determined by aligning the amino acid sequence of a protein under examination with avGFP (SEQ ID NO:24), e.g., as described in Matz et al., Nat. Biotechnol. (1999) 17: 969-973. As used herein the term "fluorescent protein" or "fluoroprotein" means a protein that is fluorescent; e.g., it may exhibit low, medium or intense fluorescence upon irradiation with light of the appropriate excitation wavelength. The fluorescent proteins of the present invention do not include proteins that exhibit fluorescence only from residues that act by themselves as intrinsic fluors, i.e., tryptophan, tyrosine and phenylalanine. As used herein, the term "fluorescent protein" also does not include luciferases, such as *Renilla* luciferase.

In fluorescent proteins of the GFP family, the chromophore is formed autocatalytically, i.e. no enzymes, cofactors and/or substrates are required for chromophore formation and fluorescence with the exception of molecular oxygen. It has been demonstrated that the green chromophore in GFP is formed by cyclization of the protein backbone in the Ser65-Tyr66-Gly67 region, followed by dehydrogenation of the $C\alpha$-$C\beta$ bond of Tyr66. As a result, a bicyclic structure of 5-(4-hydroxybenzylidene)-3,5-dihydro-4H-imidazol-4-one is formed, in which the six-member aromatic ring of the Tyr66 side chain is linked to an unusual five-member heterocycle, which itself originates from condensation of the carbonyl carbon of Ser65 with the nitrogen of Gly67 (see e.g., Heim et al., Proc Nat'l Acad. Sci. USA. (1994) 91:12501-12504; Ormo et al., Science (1996) 273:1392-1395; and Yang et al., Nat. Biotechnol. (1996) 14:1246-1251). All of the green proteins possess the avGFP-like chromophore, with modifications of protein's environment contributing to differences in the spectral shapes of these different proteins (see e.g., Brejc et al., Proc. Nat'l Acad. Sci. USA (1997) 94: 2306-2311; Palm et al., Nat. Struct. Biol. (1997) 4:361-365; and Gurskaya et al., BMC Biochem. (2001) 2:6).

In red GFP-like proteins, additional chemical modification of the GFP-like chromophore occurs. In particular, oxidation of a $C\alpha$-N bond at residue 65 (avGFP numbering) results in an acylimine group conjugated to a GFP-like core in DsRed (see Gross et al., Proc. Nat'l Acad. Sci. USA (2000) 97:11990-11995; Wall et al., Nat. Struct. Biol. (2000) 7:1133-1138; and Yarbrough et al., Proc. Nat'l Acad. Sci. USA (2001) 98:462-467). The DsRed-like chromophore is formed within many other proteins with red-shifted absorption and fluorescence (See e.g., Pakhomov, A. A. and Martynov, V. I., Chem. Biol. (2008) 15: 755-764). In some proteins, the acylimine moiety of the DsRed chromophore is further attacked by various nucleophiles to form additional types of red-shifted chromophores. For example, the chromophore in the purple chromoprotein asFP595 is formed by hydrolysis of the acylimine group, resulting in cleavage of the protein backbone and formation of a keto group conjugated to a GFP-like chromophore core (see e.g., Quillin et al., Biochemistry (2005) 44: 5774-5787; and Yampolsky et al., Biochemistry (2005) 44: 5788-5793). In the orange fluorescent proteins mOrange and mKO, nucleophilic addition of Thr65 (in mOrange) or Cys65 (in mKO) side chain groups leads to unusual heterocycles without protein backbone scission (see e.g., Shu et al., Biochemistry (2006) 45: 9639-9647 and Kikuchi et al., Biochemistry (2008) 47: 11573-11580).

Amino acid substitution of one or more residues in the chromophore and chromophore environment will strongly affect fluorescence maxima of FPs. These positions crucial for fluorescence of particular color can be found by sequence comparison of fluorescent proteins of different colors. In many cases, one amino acid substitution, i.e. corresponding to residue 65 of avGFP, is required to produce a green fluorescent protein from the red FP (see e.g., Gurskaya et al., BMC Biochemistry (2001) 2:6).

Three-dimensional structure of the GFP-like domain represents so-called β-can, a 11-stranded β-barrel enclosing an α-helix (see e.g., Ormo et al., Science (1996) 273: 1392-1395; Wall et al., Nat. Struct. Biol. (2000), 7: 1133-1138; Yarbrough et al., Proc. Nat'l Acad. Sci. USA (2001) 98: 462-467; Prescott et al., Structure (Camb) (2003) 11: 275-284; Petersen et al., J. Biol. Chem. (2003) 278: 44626-44631; Wilmann et al., J. Biol Chem (2005), 280: 2401-2404; Remington et al., Biochemistry (2005) 44: 202-212; and Quillin et al., Biochemistry (2005) 44: 5774-5787). The chromophore is located in the central region of the α-helix.

Fluorescent proteins are widely known today due to their use as fluorescent markers in biomedical sciences (see, e.g., detailed discussions in Lippincott-Schwartz and Patterson in Science (2003; 300(5616):87-91) and Stepanenko et al. in Curr Protein Pept Sci. (2008; 9(4):338-369)). They are applied for wide range of applications including the study of gene expression and protein localization (Chalfie et al., Science 263 (1994), 802-805, and Heim et al. in Proc. Nat. Acad. Sci. (1994), 91: 12501-12504), as a tool for visualizing subcellular organelles in cells (Rizzuto et al., Curr. Biology (1995), 5: 635-642), and for the visualization of protein localization and transport along the secretory pathway (Kaether and Gerdes, FEBS Letters (1995), 369: 267-271), etc.

For fluorescent proteins suitable for such uses, novel fluorescent proteins have been identified with improved fluorescence intensity and maturation rates at physiological temperatures, modified excitation and emission spectra, and reduce oligomerization and aggregation properties. In addition, mutagenesis of known proteins has been undertaken to improve their chemical properties. Finally, codon usage may be optimized for high expression in the desired heterological system, for example in mammalian cells (Haas, et al., Current Biology (1996), 6: 315-324; Yang, et al., Nucleic Acids Research (1996), 24: 4592-4593).

For deep imaging of animal tissues, the optical window favorable for light penetration is in near-infrared wavelengths, which requires proteins with emission spectra in the far-red wavelengths (Shcherbo et al., 2007; Shcherbo et al., 2009; Hoffman, Trends Biotechnol. 2008, 26(1): 1-4; Deliolanis et al., J Biomed Opt. 2008, 13(4): 044008).

Red and far-red fluorescent proteins are also important tools for multicolor labeling techniques (Chudakov et al., Trends Biotechnol. 2005; 23(12):605-613), enhanced FRET (fluorescent resonance energy transfer) techniques (Chudakov et al., Trends Biotechnol. 2005; 23(12):605-613) and visualization in living tissues (Shcherbo et al., Nat. Methods. 2007; 4(9): 741-746; Shcherbo et al., Biochem J. 2009; 418 (3): 567-74; Hoffman, Trends Biotechnol. 2008, 26(1): 1-4; Deliolanis et al., J Biomed Opt. 2008, 13(4): 044008).

Katushka (also known as TurboFP635, SEQ ID Nos: 2) is one of the brightness far-red fluorescent proteins known in the art. Katushka was produced from the red fluorescent protein from sea anemone *Entacmaea quadricolor* (Shcherbo et al., Nat Methods. 2007; 4 (9):741-6). It is dimeric protein characterized by excitation maximum at 588 nm, emission maximum at 635 nm, quantum yield 0.34, extinction coefficient 65,000 $M^{-1}$ $cm^{-1}$ (calculated brightness 22.1), and pKa 5.5.

The utility of far-red fluorescent proteins as a tool in molecular biology has prompted the search for such proteins with improved properties, as compared to known far-red fluorescent proteins. Thus, it is an object to provide novel fluorescent proteins that exhibit properties not currently available in the known fluorescent proteins, as well as DNAs encoding them.

SUMMARY OF THE INVENTION

Nucleic acid molecules encoding improved far-red fluorescent proteins obtained by mutagenesis of far-red fluorescent protein Katushka (SEQ ID Nos: 2) are provided, as well as proteins and peptides encoded by these nucleic acids. Said nucleic acid and proteins are isolated, synthesized or present in its non-natural environment.

Also provided are proteins that are substantially similar to, or derivatives, homologues, or mutants of, the specific improved far-red mutants of the Katushka. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided.

Aspects of the invention include a nucleic acid that encodes a protein that comprises a GFP-like domain, where the GFP-like domain has three-dimensional structure called β-can and comprises a functional chromophore and produces fluorescence.

In some embodiments, the fluorescent protein comprises at least one amino acid substitution that reduced protein aggregation in vitro as compared with Katushka. In some embodiments, the substitution is R201K.

In some embodiments, the protein has far-red-shifted emission spectra of fluorescence as compared with SEQ ID NO:2. In some embodiments, the fluorescent protein comprises at least one amino acid substitution located at amino acid positions corresponding to M14, L16, M44, S146, S161, R200, or L202 of SEQ ID NO:2. In some embodiments, fluorescent protein comprises substitutions at several or all positions noted above. In some embodiments, the substitution is selected from the group consisting of M14S, M14T, M14V, M14A, L16N, L16D, L16K, L16E, M44A, M44C, M44G, M44V, T63Y, S146N, S161A, S161N, M163Y, R200Y, R200F, L202Y.

In some embodiments, the GFP-like domain of the fluorescent protein shares 85% or more sequence identity with the GFP-like domain of the fluorescent protein selected from the group consisting of SEQ ID NO:2, 8, 10, 12, 14, 16, 18, and 20, i.e. residues 4-222 of any of SEQ ID NO:2, 8, 10, 12, 14, 16, 18, and 20.

In some embodiments, the GFP-like domain shares 90% or more identity, 91%, 92%, 93%, 94%, 95% or more identity, i.e. 96%, 97%, 98%, 99% or more (e.g. 100%) sequence identity to the GFP-like domain of a protein selected from the group consisting of SEQ ID NO:2, 8, 10, 12, 14, 16, 18, and 20.

In some embodiments, the fluorescent protein has a sequence identity of 85% or more to full length fluorescent protein selected from the group consisting of SEQ ID NO:2, 8, 10, 12, 14, 16, 18, and 20. In some embodiments, the protein shares 90% or more identity, 91%, 92%, 93%, 94%, 95% or more identity, i.e. 96%, 97%, 98%, 99% or more (e.g. 100%) sequence identity to fluorescent protein selected from the group consisting of SEQ ID NO: 2, 8, 10, 12, 14, 16, 18, and 20. In some embodiments, the fluorescent protein has an amino acid sequence represented by SEQ ID NO: 8, 10, 12, 14, 16, 18, or 20. In some embodiments, the nucleic acid encoding the fluorescent protein has a nucleotide sequence represented by SEQ ID NO: 7, 9, 11, 13, 15, 17, or 19.

In some embodiment the fluorescent protein comprises one or more substitutions that provides for at least one altered spectral or biochemical property as compared with SEQ ID NO:2, wherein the property is oligomerization capacity, pH stability, photostability, absorbance spectrum, fluorescence excitation spectrum, fluorescence emission spectrum, fluorescence brightness, protein folding, and/or chromophore maturation rate. For example, the fluorescent protein can comprise D24G and\or T9S folding substitutions.

Additional aspects of the invention include proteins that are encoded by the subject nucleic acids. In some embodiments, the protein comprises a GFP-like domain, where the GFP-like domain comprises a functional chromophore, i.e. produces fluorescence or color, and forms β-can three-dimensional structure. In some embodiments, the protein has far-red-shifted emission spectra of fluorescence as compared with SEQ ID NO:2. In some embodiments, the fluorescent protein comprises at least one amino acid substitution located at amino acid positions corresponding to M14, L16, M44, S146, S161, R200, or L202 of SEQ ID NO:2. In some embodiments, fluorescent protein comprises substitutions at several or all positions noted above. In some embodiments, the substitution is selected from the group consisting of M14S, M14T, M14V, M14A, L16N, L16D, L16K, L16E, M44A, M44C, M44G, M44V, T63Y, S146N, S161A, S161N, M163Y, R200Y, R200F, L202Y.

In some embodiments, the fluorescent protein comprises at least one amino acid substitution that reduced protein aggregation in vitro as compared with Katushka. In some embodiments, the substitution is R201K. In some embodiments, said substitutions is combined with at least one substitution at amino acid positions corresponding to M14, L16, M44, S146, S161, R200, or L202 of SEQ ID NO:2.

In some embodiments, the GFP-like domain of the fluorescent protein shares 85% or more sequence identity with the GFP-like domain of the fluorescent protein selected from the group consisting of SEQ ID NO:2, 8, 10, 12, 14, 16, 18, and 20, i.e. residues 4-222 of any of SEQ ID NO:2, 8, 10, 12, 14, 16, 18, and 20. In some embodiments, the GFP-like domain shares 90% or more identity, 91%, 92%, 93%, 94%, 95% or more identity, i.e. 96%, 97%, 98%, 99% or more (e.g. 100%) sequence identity to the GFP-like domain of a protein selected from the group consisting of SEQ ID NO:2, 8, 10, 12, 14, 16, 18, and 20.

In some embodiments, the fluorescent protein has a sequence identity of 85% or more to full length fluorescent protein selected from the group consisting of SEQ ID NO:2, 8, 10, 12, 14, 16, 18, and 20. In some embodiments, the protein shares 90% or more identity, 91%, 92%, 93%, 94%, 95% or more identity, i.e. 96%, 97%, 98%, 99% or more (e.g. 100%) sequence identity to fluorescent protein selected from the group consisting of SEQ ID NO: 2, 8, 10, 12, 14, 16, 18, and 20. In some embodiments, the fluorescent protein has an amino acid sequence represented by SEQ ID NO: 8, 10, 12, 14, 16, 18, or 20. In some embodiments, the nucleic acid encoding the fluorescent protein has a nucleotide sequence represented by SEQ ID NO: 7, 9, 11, 13, 15, 17, or 19.

In some embodiment the fluorescent protein comprises one or more substitutions that provides for at least one altered spectral or biochemical property as compared with SEQ ID NO:2, wherein the property is oligomerization capacity, pH stability, photostability, absorbance spectrum, fluorescence excitation spectrum, fluorescence emission spectrum, fluorescence brightness, protein folding, and/or chromophore maturation rate. For example, the fluorescent protein can comprise D24G and\or T9S folding substitutions.

Additional aspects of the invention include vectors containing the nucleic acids of the present invention. Included also are expression cassettes comprising a nucleic acid of the present invention and regulatory elements necessary for expression of the nucleic acid in the desired host-cell. Included also are fusion proteins and nucleic acids encoding the same comprising the subject fluorescent protein or mutant thereof.

Additional aspects of the invention include methods of producing a subject fluorescent protein, by expressing of a protein in a suitable host cell and isolating the protein from that cell. In some embodiments, the method includes the steps of (a) contacting a host cell with a nucleic acid molecule of the present invention operably linked to one or more expression regulatory elements, (b) expressing the fluorescent protein from the nucleic acid molecule, and (c) isolating the protein substantially free from other proteins.

In addition, antibodies specifically binding to the proteins of the present invention or fragments thereof are provided.

Additionally, host-cells, stable cell lines, transgenic animals and transgenic plants comprising nucleic acids, vectors or expression cassettes of the present invention are provided.

Also provided are methods that use a fluorescent protein of the present invention or the nucleic acid encoding it.

Additionally, kits comprising nucleic acids or vectors or expression cassettes harboring the nucleic acids, or proteins of the present invention are provided.

Also provided are methods of producing a fluorescent protein of the present invention comprising expressing of a protein in a suitable host-cell and isolating the protein therefrom.

BRIEF DESCRIPTION OF THE DRAWINGS

Figure 1:
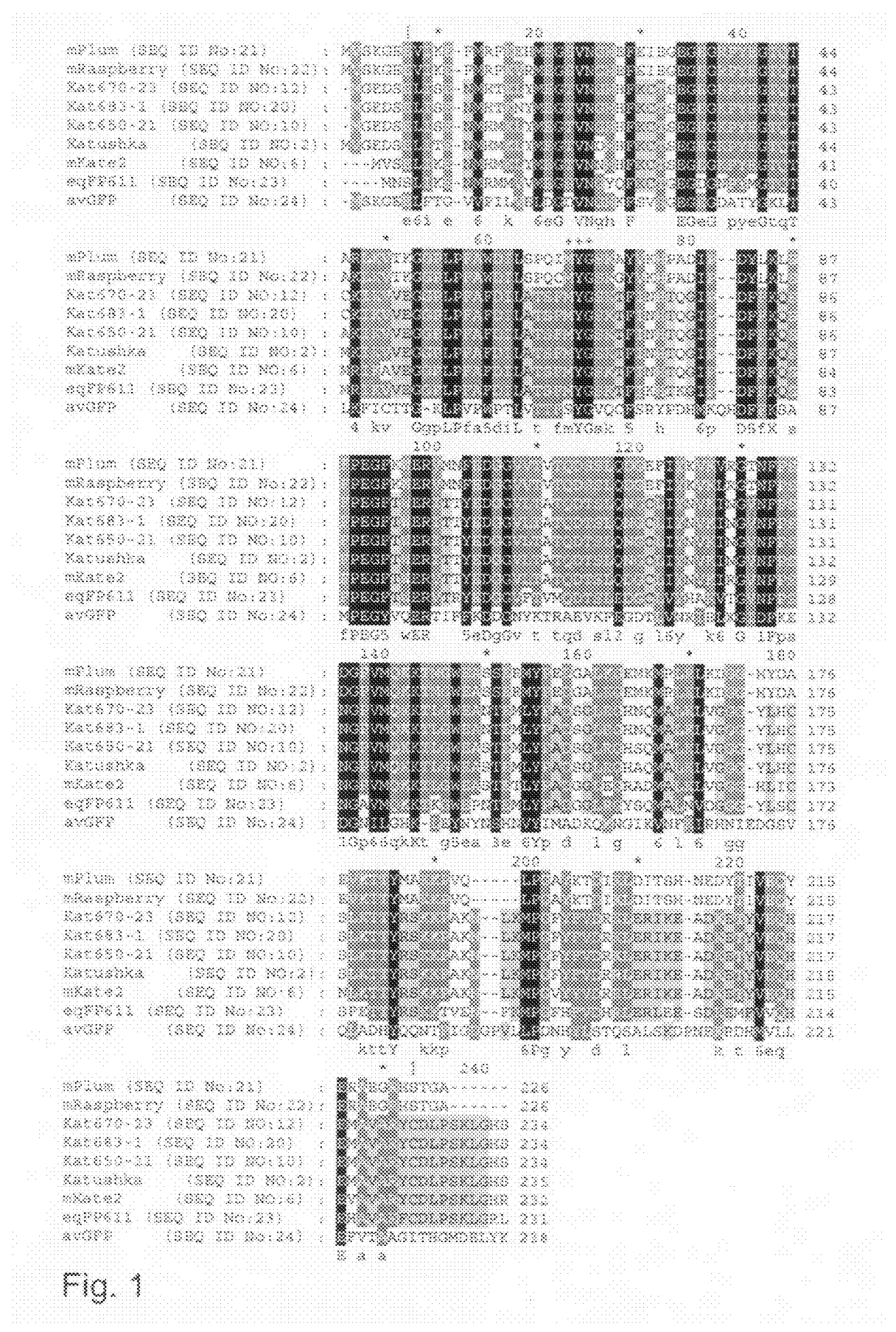

FIG. 1 shows sequence alignments of exemplary novel fluorescent proteins with avGFP (SEQ ID No:24) and known far-red fluorescent proteins including Katushka (SEQ ID NO:2), mKate2 (SEQ ID NO:6), mPlum (SEQ ID No:21), mRaspberry (SEQ ID No:22), and eqFP611 (SEQ ID No:23). Introduced gaps are shown by dots. Conservative amino acids are marked by black. GFP-like domain start and finish are specified at the top by square brackets ("[" and "]") Amino acid residues that form chromophore is marked by pluses ("+++").

DETAILED DESCRIPTION

Figure 2:
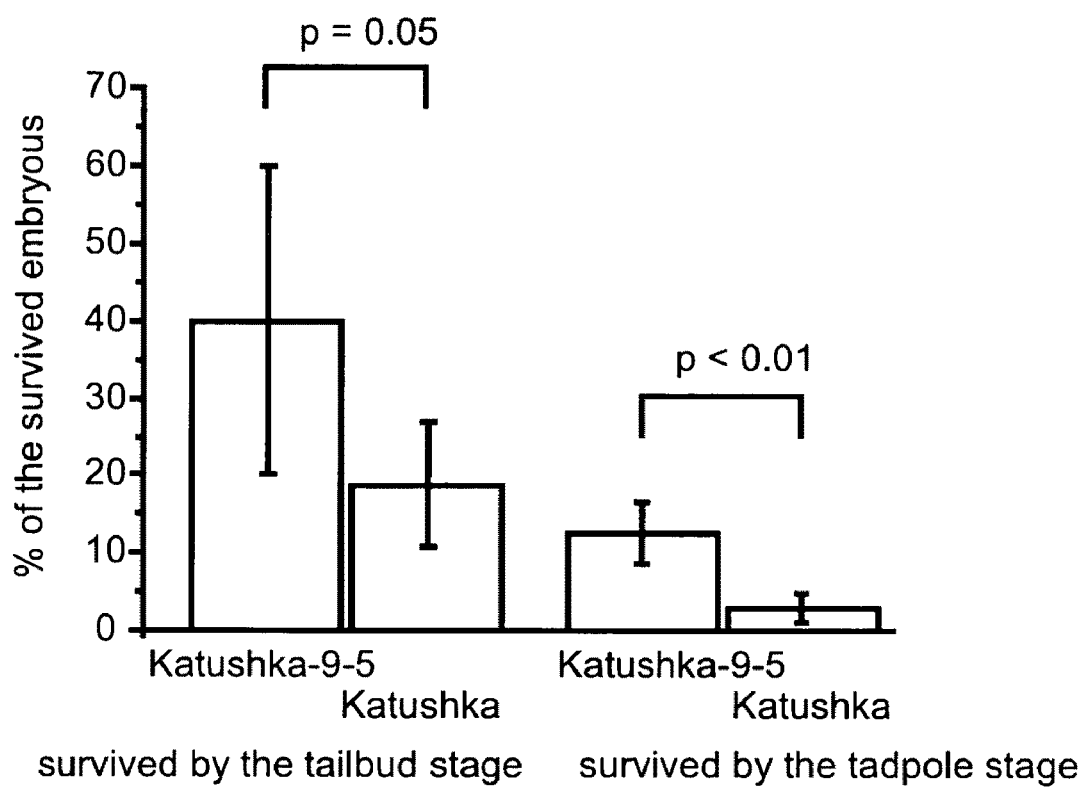
FIG. 2 illustrates Katushka and Katushka-9-5 cytotoxicity in microinjected *Xenopus laevis* embryos. Percentages of surviving embryos by the tailbud and tadpole stages, respectively, are shown.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention is directed to nucleic acid molecules encoding improved fluorescent mutants of the Katushka protein, variants and derivatives thereof, and proteins and peptides encoded by these nucleic acids. Also provided are vectors and expression cassettes comprising these nucleic acids, and stable cell lines, transgenic animals, and transgenic plants comprising these nucleic acids, vectors or expression cassettes. Also provided are methods of producing these fluorescent proteins and mutants thereof, and antibodies specifically binding to these fluorescent proteins and mutants or fragments thereof. Also provided are methods that use a fluorescent protein of the present invention or the nucleic acid encoding it. Additionally, kits comprising nucleic acids or vectors or expression cassettes harboring the nucleic acids, or proteins of the present invention are provided.

Nucleic Acid Molecules

The present invention provides nucleic acid molecules that comprise nucleotide sequences encoding fluorescent mutants of Katushka protein. A nucleic acid molecule as used herein is DNA molecules, such as genomic DNA molecules or cDNA molecules, or RNA molecules, such as mRNA molecules. In particular, the nucleic acid molecule is a cDNA molecule having an open reading frame that encodes a fluorescent protein of the invention and is capable, under appropriate conditions, of being expressed as a fluorescent protein according to the invention. The invention also encompasses nucleic acids that are homologous, substantially similar to, identical to, derived from, or mimetics of the nucleic acids encoding proteins of the present invention. The subject nucleic acids are present in an environment other than their natural environment; e.g., they are isolated, present in enriched amounts, or are present or expressed in vitro or in a cell or organism other than their naturally occurring environment.

Specific nucleic acid molecules of interest include nucleic acid molecules that encode the following fluorescent proteins, and homologs/derivates/mutants thereof: Kat650-21 (SEQ ID NO:10), Kat670-23 (SEQ ID NO:12), KatX1 (SEQ ID NO:14), KatX2 (SEQ ID NO:16), Katushka 9-5A (SEQ ID NO:18), and Kat683-1 (SEQ ID NO:20).

The deduced cDNA coding sequences for these proteins are the following: Kat650-21 (SEQ ID NO:9), Kat670-23 (SEQ ID NO:11), KatX1 (SEQ ID NO:13), KatX2 (SEQ ID NO:15), Katushka 9-5A (SEQ ID NO:17), Kat683-1 (SEQ ID NO:19).

Each of these particular types of nucleic acid molecules of interest is discussed below and in the experimental section.

In addition to the above described specific nucleic acid compositions, also of interest are homologues of the above sequences. With respect to homologues of the subject nucleic acids, the source of homologous genes may be any species of plant or animal or the sequence may be wholly or partially synthetic (e.g. genetically engineered). In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 contiguous nucleotides long, more usually at least about 30 contiguous nucleotides long, and may extend to the complete sequence that is being compared. Algorithms for sequence analysis are known in the art, such as BLAST, described in Altschul et al. (1990), J. Mol. Biol. 215:403-10 (using default settings, i.e. parameters w=4 and T=17). The sequences provided herein are essential for recognizing related and homologous nucleic acids in database searches. Of interest in some embodiments are nucleic acids of substantially the same length as the nucleic acid identified as SEQ ID NOS:3, 7, 9, 11, 13, 15, 17, and 19, where by substantially the same length is meant that any difference in length does not exceed about 10%, usually does not exceed about 5% and more usually does not exceed about 2%; and have sequence identity to any of these sequences of about 90% or more, usually at least about 95% and more, usually at least about 99% over the entire length of the nucleic acid. In many embodiments, the nucleic acids have a sequence that is substantially similar (i.e. the same as) or identical to the sequences of SEQ ID NOS: 3, 7, 9, 11, 13, 15, 17, and 19. By substantially similar is meant that sequence identity will generally be at least about 90%, usually at least about 95% and often at least about 96%, 97%, 98%, or even 99%.

Mutants or derivates can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any convenient method, including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and combinations thereof (see, for example, Gustin et al., Biotechniques (1993) 14: 22; Barany, Gene (1985) 37: 111-123; Colicelli et al., Mol. Gen. Genet. (1985) 199:537-539; and Sambrook et al., Molecular Cloning: A Laboratory Manual, (1989), CSH Press, pp. 15.3-15.108). In some embodiments, fluorescent proteins encoded by mutant or derived nucleic acids have the same fluorescent or biochemical properties as the initial fluorescent protein. In other embodiments, mutant or derived nucleic acids encode fluorescent proteins with altered properties, e.g., they can have altered photostability, oligomerization state, excitation and emission spectra, quantum yield, extinction coefficient.

In addition, degenerate variants of the nucleic acids that encode the proteins of the present invention are also provided. Degenerate variants of nucleic acids are nucleic acids in which the amino-acid encoding codons are replaced with other codons encoding the same amino acids. For example, degenerate variants of a nucleic acid are generated to increase its expression in a host cell. In this embodiment, codons of the nucleic acid that are non-preferred or are less preferred in the host cell are replaced with the codons over-represented in coding sequences in genes in the host cell, wherein the replaced codons encodes the same amino acid. Humanized versions of the nucleic acids of the present invention are under particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins, the disclosure of which is herein incorporated by reference. Examples of degenerated variants of interest are described in more details in experimental part, infra.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' non-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the fluorescent proteins having amino acid sequences represented by SEQ ID NOs: 8-20 or mutants thereof. In certain embodiments, the nucleic acid molecules encodes complete or truncated (minimum) GFP-like domains of the subject proteins that are capable to be fluorescent when expressed in vitro and\or in vivo. GFP-like domains are described further below.

Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 contiguous nucleotides or greater in length (e.g. 642 bp or 660 bp long). In some embodiments, the DNA fragment shares 50%, 55%, 60%, 65%, 70%, 75% or more sequence identity with a fragment of the subject nucleic acid, e.g. 80%, 85%, or 90% or more identity, more often 92%, 95%, 96%, 97%, 99% or more, e.g. 100% identity with a fragment of the subject nucleic acid that is about 15 contiguous nucleotides in length, about 18 contiguous nucleotides in length, about 25 contiguous nucleotides in length, about 50 contiguous nucleotides in length. In some embodiments, the subject nucleotide acid molecule fragment may be about 100, about 200, about 300, about 400, about 500, about 600, about 700 contiguous nucleotides or greater in length (e.g. 642 bp or 660 bp long).

The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids, 214 amino acids; 215 amino acids; 217 amino acids; 218 amino acids; 219 amino acids; 220 amino acids; up to the full length protein.

The subject nucleic acids may be isolated and obtained in substantially purified form. Substantially purified form means that the nucleic acids are at least about 80% pure, usually at least about 90% pure and are typically "recombinant", i.e., flanked by one or more nucleotides with which they are not normally associated on a naturally-occurring chromosome in a natural host organism.

The nucleic acids of the present invention, e.g. the corresponding cDNAs, full-length genes and constructs can be generated synthetically by a number of different protocols known to those of skill in the art. Appropriate nucleic acid constructs are purified using standard recombinant DNA techniques as described in, for example, Sambrook et al., Molecular Cloning: A Laboratory Manual, 2nd Ed., (1989) Cold Spring Harbor Press, Cold Spring Harbor, N.Y., and under regulations described in, e.g., United States Dept. of HHS, National Institute of Health (NIH) Guidelines for Recombinant DNA Research.

Also provided are nucleic acids that encode fusion proteins comprising a fluorescent protein of the present invention are also provided and discussed in more detail below.

Also provided are vectors and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject fluorescent proteins or fusion proteins thereof or for replication of the subject nucleic acid molecules. The expression cassette may exist as an extrachromosomal element or may be integrated into the genome of the cell as a result of introduction of the expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operably linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g. the co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus* oocytes, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also of interest are promoter sequences of the genomic sequences of the present invention, where the sequence of the 5' flanking region may be utilized for promoter elements, including enhancer binding sites, that, for example, provide for regulation of expression in cells/tissues where the subject proteins gene are expressed.

Also provided are small DNA fragments of the subject nucleic acids that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

The subject nucleic acids, including flanking promoter regions and coding regions, may be mutated in various ways known in the art to generate targeted changes in promoter strength or to vary the sequence of the encoded protein or properties of the encoded protein, including the fluorescent properties of the encoded protein.

Proteins

Also provided by the subject invention are fluorescent proteins, derivates, and mutants thereof including full-length proteins, as well as portions or fragments thereof.

As discussed above, specific fluorescent proteins of interest include the following fluorescent proteins: Katushka 9-5 (SEQ ID NO:8), Kat650-21 (SEQ ID NO:10), Kat670-23 (SEQ ID NO:12), KatX1 (SEQ ID NO:14), KatX2 (SEQ ID NO:16), Katushka 9-5A (SEQ ID NO:18), and Kat683-1 (SEQ ID NO:20). Also of interest are mutants and fragments thereof, e.g. fragments comprising the GFP-like domain, as described further below.

Homologs that vary in sequence from the above provided specific amino acid sequences of the subject invention, i.e., SEQ ID NOs: 2, 8, 10, 12, 14, 16, and 18 are also provided. By homolog is meant a protein having 50% or more, usually 55% or more and more usually 60% or more amino acid sequence identity to amino acid sequences of referred protein as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5). In many embodiments, homologs of interest have much higher sequence identity e.g., 70% or more, 75% or more, 80% or more, 85% or more, 90% or more (e.g., 92% or more, 93% or more, 94% or more), e.g., 95% or more, 96% or more, 97% or more, 98% or more, 99% or more, or 99.5%, particularly for the amino acid sequence that provides the functional regions of the protein.

Also provided are proteins that are substantially identical to the proteins of SEQ ID NOs: 2, 8, 10, 12, 14, 16, and 18 where by substantially identical is meant that the full-length protein or fragment thereof (e.g. complete or minimum (truncated) GFP-like domain) has an amino acid sequence identity to the sequence of reference protein or fragment of 90% or more, usually 92% or more, and more usually 95% or more, where in some instances the identity may be much higher, e.g., at least 96%, at least 97%, at least 98%, at least 99% or higher.

In some embodiments, subject proteins and mutants thereof range in length from about 150 to 300 amino acids, more usually from about 200 to 250 amino acid residues. In some embodiments, the subject proteins and mutants thereof have a molecular weight ranging from about 15 to 35 kDa, more usually from about 17.5 to 32.5 kDa, where the molecular weight is the average molecular weight, i.e. the calculated molecular weight based upon the average weight for amino acids of 0.11 kD per amino acid.

In some embodiments, the subject proteins are bright, where by bright is meant that they exhibit fluorescence that can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient.

In some embodiments, the subject proteins and mutants thereof demonstrate particular fluorescent, or spectral, properties. "Fluorescent property" or "spectral property" is used to refer to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties of reference protein in different conditions is useful. A measurable difference can be determined as the amount of any quantitative fluorescent property, e.g., the amount of fluorescence at a particular wavelength, or the integral of fluorescence over the emission spectrum. In some embodiments, the subject proteins or mutants thereof have an excitation maximum ranging from about 500 nm to 700 nm, usually from about 550 nm to 630 nm and more usually from about 570 to 620 nm, and often from about 550 to 620 nm, while the maximum of emission spectra of the subject proteins typically ranges from about 600 nm to 800 nm, usually from about 630 nm to 700 nm and more usually from about 640 to 690 nm while in many embodiments the maximum of emission spectra ranges from about 630 to 685 nm. The subject proteins generally have a maximum extinction coefficient that ranges from about 25,000 to 150,000 $cm^{-1}$ $mol^{-1}$ and usually from about 45,000 to 140,000 $cm^{-1}$ $mol^{-1}$, e.g., 50,000 to 130,000 $cm^{-1}$ $mol^{-1}$. The subject proteins generally have a quantum yield that ranges from about 0.04 to 0.8, usually from 0.05 to 0.4, e.g. from 0.15 to 0.3. A fluorescence spectrophotometer (e.g. Varian Cary Eclipse Fluorescence Spectrophotometer, or spectrophotometer SMS 2 VIS built into the stereomicroscope Olympus SZX-12) can be used for measuring excitation-emission spectra, with wavelength corrections if appropriate.

In some embodiments, the subject fluorescent proteins possess a GFP-like domain that is homologous to the GFP-like domain of Green Fluorescent Protein from *A. victoria* (avGFP) (SEQ ID NO:24), e.g GFP-like domain having 20% or more, usually 25% or more and more usually 30% or more amino acid sequence identity to amino acid sequences of referred GFP-like domain of avGFP as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5).

Alternatively, GFP-like domain can be identified in the amino acid sequences of the subject proteins using available software for analysis of domain organization, for example using Conserved Domain Database (CDD, website identifiable by placing "http://www" in front of "ncbi.nlm.nih.gov/Structure/cdd/") and Simple Modular Architecture Research Tool (SMART, website identifiable by placing "http://" in front of smart.embl-heidelberg.de/). The minimum GFP-like domain of the subject nucleic acids is that portion of the GFP-like domain that is necessary and sufficient for the protein to mature and demonstrate fluorescence. In other words, the minimum GFP-like domain is responsible for the fluorescence of the protein.

Sequence alignments of subject proteins with avGFP, DsRed or mutants thereof, e.g. mPlum (SEQ ID NO:21) and mRaspberry (SEQ ID NO:22), can be used to identify the starts and the ends of the GFP-like domain and minimum GFP-like domain (i.e. core sequence that is necessary and sufficient for the maturation and fluorescence of the subject fluorescent proteins). Multiple alignment of the sequences can be performed using the Clustal method of alignment (Higgins and Sharp, CABIOS. 5:151153 (1989)) with default parameters (GAP PENALTY=10, GAP LENGTH PENALTY=10), unless otherwise specified. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

In some embodiments, the GFP-like domain of the subject protein begins at the amino acid residue corresponding to the position 6 of avGFP as identified using sequence alignment of a fluorescent protein under examination and avGFP (SEQ ID NO:24), e.g. residue 7 of SEQ ID NO:2. In some embodiments, the GFP-like domain ends at the amino acid residue corresponding to the position 227 of avGFP, e.g. residue 224 of SEQ ID NO:2. In some embodiments, the minimum GFP-like domain is a GFP-like domain that is truncated at its N-terminus, beginning, for example, at a residue corresponding to residue 7, 8, or 10 of avGFP, e.g. residue 8, 9, or 11 of SEQ ID NO:2 and mutants thereof (e.g. SEQ ID NO: 8, 10, 12, 14, 16, 18, 20). In some embodiments, the minimum GFP-like domain is a GFP-like domain that is truncated at its C-terminus, ending, for example, at a residue corresponding to residue 233, 230, or 227 of avGFP, e.g. residue 230, 227, or 224 of SEQ ID NO:2 and mutants thereof (e.g. SEQ ID NO: 8, 10, 12, 14, 16, 18, 20). In some embodiments, the minimum GFP-like domain is 200 amino acids long or more, more usually about 215 amino acids long, and more usually at least 219 amino acids long (e.g. 219; 220; 221; 222; 223; 224; 225; 230; 231; 232; 233 amino acids long). Accordingly, in some embodiments, the GFP-like domain of SEQ ID NO:2 may begin, for example, at about residue 7 to about amino acid residue 226, where the minimum GFP-like domain may begin at about residue 8 and end at about residue 226, or may begin at about residue 9 and end at about residue 228. In some embodiments, the minimum GFP-like domain of SEQ ID NO:2 and mutants thereof extends from residue 8 to residue 224.

Also provided are proteins that have a GFP-like domain that is homologous to the GFP-like domain of fluorescent proteins of SEQ ID NOs: 2, 8, 10, 12, 14, 16, 18, or 20, whereby homologous it is meant sharing a sequence identity that is 50% or more, 55% or more, or 60% or more with the GFP-like domain of a reference protein interest, and in some cases, having much higher sequence identity e.g., 70% or more, 75% or more, 80% or more, 85% or more, 90% or more (e.g., 91% or more, 92% or more, 93% or more, 94% or more), e.g., 95% or more, 96% or more, 97% or more, 98% or more, 99% or more, or 99.5%. In some embodiments, the proteins have a GFP-like domain that is substantially identical to the GFP-like domain of the reference protein, e.g. SEQ ID NOs: 2, 8, 10, 12, 14, 16, 18, or 20, where by substantially identical it is meant sharing a sequence identity to the GFP-like domain of the subject protein of at least 90% and more usually at least about 95%, where in some instances the identity may be much higher, e.g., at least 96%, at least 97%, at least 98%, at least 99% or higher.

Fluorescent proteins that are mutants of the above-described proteins, that fluoresce, i.e. emit fluorescence, are also provided. In some embodiments, the mutations are substitutions, deletions or insertions of one or more amino acids. It is well known in the art that, barring substitution of the amino acid residues that are strictly conserved across members of the GFP family of proteins, e.g. some residues of the chromophore and chromophore environment (i.e. corresponding to residues 67 and 96 of avGFP), a high degree of mutation may be tolerated. For example, substitutions corresponding to positions 6, 9, 14, 16, 24, 44, 146, 161, 200, 202, and 201 of SEQ ID NOS:2, 8, 10, 12, 14, 16, 18, and 20 may be made without destroying fluorescence. Additional substitutions that can be introduced into the subject proteins without destroying fluorescence are described for example in U.S. Pat. No. 7,638,615. Other examples of residues that may be substituted may be readily identified by cross-referencing alignments made between known members of the GFP family that identify strictly conserved residues, e.g. as provided in FIG. 1 of the accompanying drawings, with the teachings of the structure for GFP disclosed in by Yang et al (1996) Nature Biotechnology 14:1246-1251, Ormo et al. (1996) Science 273:1392-1395, and Matz et al. (1999) Nature Biotechnology 17:969-973, the entire disclosures of which are incorporated herein, and by performing alignments such as that provided in FIG. 1 of the accompanying drawings.

Additional amino acid residues within and flanking the GFP-like domain and minimum GFP-like domain that may be substituted in the subject proteins without loss of fluorescence are readily identifiable by performing sequence alignments with avGFP, DsRed (or its mutants) and other known fluorescent proteins as discussed above.

In some embodiments, mutants and variants retain biological properties of the initial proteins (e.g. proteins subjected for mutagenesis). In some embodiments, mutants and variants have biological properties which differ from the initial proteins. The term "biological property" of the proteins of the present invention refers to, without limitation, spectral properties, such as absorbance maximum, emission maximum, maximum extinction coefficient, brightness (e.g., as compared to the reference protein such mKate2 protein), and the like; and biochemical properties, such as in vivo and/or in vitro stability (e.g., half-life), sensitivity to pH, maturation speed, aggregation and/or oligomerization tendency, and other such properties.

In some embodiments, the subject proteins has reduced tendency to aggregate as compared with Katushka protein. The difference in aggregation capacity can be monitored in vitro for the purified protein samples by detection of visible aggregates in the protein samples with concentration of about 10 mg/ml or higher after 48 hours incubation at 4 degree C. For example, at concentration of 10 mg/ml Katushka forms visible aggregates after 48 hours incubation at 4 degree C. Katushka-9-5 does not form visible aggregates in identical conditions. In some embodiments, the mutation is R201K of SEQ ID NO:2. If the protein of interest is not SEQ ID NO:2, it can comprise 201K in the position 201, where the number is the position in the protein of interest corresponding to the position in SEQ ID NO:2, and the letter represents the amino acid that is present in at that position.

In some embodiments, the subject protein comprises one or more substitutions that shifts the fluorescence emission maximum of the protein in to the far-red spectrum as compared with Katushka, i.e. subject protein has emission maximum from about 640 nm to 750 nm, usually from about 645 nm to 710 nm and more usually from about 650 to 690 nm while in many embodiments the maximum of emission spectra ranges from about 640 to 685 nm.

In some embodiments, the protein comprises one or more substitutions at positions corresponding to M14, L16, M44, S146, S161, R200, or L202 of SEQ ID NO:2, i.e. at least one, at least two, at least three, at least four, at least five, at least six or seven substitutions at the positions corresponding to M14, L16, M44, S146, S161, R200, or L202 of SEQ ID NO:2. In some embodiments, the substitution is M14S, M14T, M14V, M14A, L16N, L16D, L16K, L16E, M44A, M44C, M44G, M44V, T63Y, S146N, S161A, S161N, M163Y, R200Y, R200F, or L202Y. In some embodiments, the protein of interest comprises one or more amino acid residues selected from the group of 14S, 14T, 14V, 14A, 16N, 16D, 16K, 16E, 44A, 44C, 44G, 44V, 63Y, 146N, 161A, 161N, 163Y, 200Y, 200F, or 202Y at the positions corresponding to the position 14, 16, 44, 146, 161, 200, or 202 in SEQ ID NO:2, where the number is the position in the protein of interest, and the letter represents the amino acid that is present in at that position.

In some embodiments, the subject protein comprises a mutation that provides for a rapid rate of folding and maturation upon expression in the host cell. By rapidly folding and maturing rate it is meant that the protein achieves a tertiary structure that gives rise to its fluorescent quality in a short period of time. In these embodiments, the proteins folds and matures with a half-life that generally does not exceed about 48 hours, usually does not exceed about 12 hours and more usually does not exceed about 3 hours. To measure the maturation rate, transformed E. coli cells (XL1 Blue strain) expressing appropriate mutant protein may be grown overnight in LB supplemented with ampicillin and 2% D-glucose. Tubes are filled to the rim and sealed upon induction to restrict oxygen availability. The bacterial cultures are centrifuged and the cell pellets re-suspended in 20 mM Tris-HCl, 100 mM NaCl, pH 7.5 buffer and lysed by sonication. The recombinant proteins are purified using TALON metal-affinity resin (Clontech). Maturation is performed at 37° C., in 35 mM KCl, 2 mM $MgCl_2$, 50 mM Tris pH 7.5, 1 mM DTT. A Varian Cary Eclipse Fluorescence Spectrophotometer or spectrophotometer SMS 2 VIS built into the stereomicroscope Olympus SZX-12 can be used for measuring maturation kinetics by monitoring growth of fluorescent signal. In some embodiments, the mutation that provides for a rapid rate of folding and maturation is a substitution at a position corresponding to D24 and T9. In some embodiments, the substitution is D24G and T9S.

In some embodiments, the subject proteins are photostable. As used herein, "photostability" is stability of protein fluorescence upon light irradiation under excitation wavelength. As used herein, "photobleaching" means the photochemical destruction of a fluorophore (chromophore) of fluorescent protein. Photostability rate is defined as a relative photobleaching speed. Photostability and photobleaching are characterized by fluorescence intensity decrease in course of irradiation by light of excitation wavelength and certain intensity.

There are several methods known in the art to measure photobleaching and photostability. See, for example, methods described by Chiu et al. (J. Neurosci. Methods (2001), 105, 55-63), Wiedenmann et al. (Proc Natl Acad Sci USA. (2002) 99, 11646-11651), Rettig et al. (Springer-Verlag, 1999, p. 206-207) and Shaner et al. (Nat Biotechnol. (2004), 22(12):1567-1572; Nat Methods. 2005; 2(12):905-909), the disclosures of which are incorporated herein. For example, photostability may be compared in living cells transiently transfected with a mutant fluorescent protein. Wide-field and laser scanning confocal microscopy photobleaching comparisons are performed, and the half-time of fluorescence decay is compared for various proteins in identical conditions of irradiation. The fluorescence intensity of a cell is measured before and after bleaching by extensive irradiation with excitation light. After several rounds of sequential detection-bleaching (usually after 10-300 rounds, more usually after 20-200 rounds, and preferable after 30-100 rounds) bleaching curves are prepared using data obtained from detecting channel of the microscope and appropriate software. The half-time of fluorescence decay (i.e. irradiation duration needed to halve fluorescence intensity relative to the initial level) is then extrapolated from bleaching curves.

For example, a Leica AF6000 LX imaging system based on a DMI 6000 B inverted microscope can be used for photostability measurements of fluorescent proteins in host-cells with 63× immersion oil objective (effective magnification ratio 630×). GFP filter cube can be used for green fluorescent proteins and TX2 filter cube can be used for red fluorescent proteins. The field of view (containing several fluorescent cells) is selected and irradiated with appropriate filter set in series of detecting (e.g., intensity 1, gain 1, exposure length 10-100 ms) and bleaching (e.g. intensity 5, gain 1, exposure length 5 s) exposures. After 30-100 frames of detection/bleaching, one can draw the bleaching curves using data from detecting channel and appropriate software. Bleaching curves are normalized and compared. Longer photobleaching half-time means higher photostability.

Detecting light allows one to measure the fluorescence signal value. It is a relatively low intensity light of fluorescence excitation wavelength. An intensity of detecting light should be calibrated with the output signal value in such a way as to fit this value into the dynamic range of CCD detector used. In each particular case detecting light intensity depends on the initial fluorescence brightness, microscope, detector and excitation light source type. Also detecting light does not considerably bleach the fluorescence (or its bleaching ability is as low as possible).

As used herein, "bleaching light" means a relatively high intensity (for example 1W/cm2) light of fluorescence excitation wavelength. Its intensity may be chosen as a maximum available with a particular microscope. Output signal usually does not matter and is not acquired for the further calculations. Bleaching light should provide the effective bleaching of fluorescence (bleaching is controlled by the detecting channel data respectively). In some cases, one can use bleaching light for both fluorescent protein bleaching and fluorescence signal measurement.

In some embodiments, the subject protein is pH stable, i.e. it has a pKa from about 2 to 7, usually from about 3 to 6 and more usually from about 4 to 6. pH titrations are performed by using a series of buffers in the pH range from 3 to 10. For each pH value, an aliquot of purified protein is diluted in an equal volume of the corresponding buffer solution and the fluorescence brightness is measured after 1 h incubation at room temperature. For accuracy, the actual pH is measured in each sample using a microelectrode (Sartorius).

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g. biochemical, spectral, etc.) property has been altered. For example, mutations that reduce aggregation of a fluorescent protein can be combined with mutations that improve protein folding and/or alter protein excitation/emission spectra, etc.

For screening of mutant variants, nucleic acids encoding these variants are cloned into suitable expression vector (for example pQE30 vector, Qiagen) and expressed in host cells (for example in E. coli XL1 Blue strain, Invitrogen). Depending on the complexity of library, from 100 to 100,000 individual clones each expressing individual FP variant are screened using a fluorescent stereomicroscope equipped with the appropriate filter set (excitation filter 545-580 nm, emission filter 610LP or 650LP). Fluorescence intensity can be also measured using a spectrophotometer at various excitation wavelengths.

The proteins of the subject invention are separated from their naturally-occurring environment. For example, purified protein is provided, where "purified" means that the protein is present in a mixture that is substantially free of non-chromogenic or fluorescent proteins of interest, where "substantially free" means that less than 90%, usually less than 60% and more usually less than 50% of the mixture content is non-chromogenic or fluorescent proteins or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In some embodiments, the proteins are present in substantially purified form, where by "substantially purified form" means at least 95%, usually at least 97% and more usually at least 99% pure.

The subject proteins and polypeptides may be synthetically produced. For example, wild type proteins may be derived from biological sources which express the proteins. The subject proteins may be derived from synthetic means, e.g. by expressing a recombinant nucleic acid coding sequence encoding the protein of interest in a suitable host, as described above. Any convenient protein purification procedures may be employed, where suitable protein purification methodologies are described in Guide to Protein Purification, (Deuthser ed., Academic Press, 1990). For example, a lysate may be prepared from the original source and purified using HPLC, exclusion chromatography, gel electrophoresis, affinity chromatography, and the like.

The subject proteins typically range in length from about 150 to 300 amino acids and usually from about 200 to 300 amino acid residues, and generally have a molecular weight ranging from about 15 to 35 kDa, usually from about 17.5 to 32.5 kDa. Also provided are fusion proteins comprising a protein of the present invention, fused, for example, to a degradation sequence, a sequence of subcellular localization (e.g. nuclear localization signal, peroximal targeting signal, Golgi apparatus targeting sequence, mitochondrial targeting sequence, protein with known subcellular localization, etc.), a signal peptide, or any protein or polypeptide of interest. Fusion proteins may include for example, a fluorescent protein of the subject invention or mutant thereof and a second polypeptide ("the fusion partner") fused in-frame at the N-terminus and/or C-terminus of the fluorescent protein. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the fluorescent protein portion of the fusion protein.

Fusion proteins can be produced using recombinant technologies well known in the art. To generate fusion proteins, a nucleic acid encoding a subject protein is operatively linked with the nucleic acid encoding "fusion partner". In the resulted nucleic acid coding sequence of the fluorescent protein and coding sequence of the "fusion partner" are covalently linked so that no frameshifts and stop codons are present between these coding sequences.

Also provided are antibodies that bind specifically to the subject fluorescent proteins and mutants thereof. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, F(ab')$_2$ and Fab are also of interest.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g. *Escherichia coli, Streptomyces* sp., *Bacillus subtilis, Lactobacillus acidophilus*, etc) or eukaryotic host-cells. Transgenic organism of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e. DNA) into such organisms are widely known and provided in references such as Sambrook et al. (Molecular Cloning: A Laboratory Manual, 3rd Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example, yeast. Yeast is widely used as a vehicle for heterologous gene expression (for example see Goodey et al Yeast biotechnology, D R Berry et al, eds, (1987) Allen and Unwin, London, pp 401-429) and by King et al Molecular and Cell Biology of Yeasts, E F Walton and G T Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2203) San Diego Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, where the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896;

5,576,198; 5,538,879; 5,484,956; the disclosures of which are herein incorporated by reference. Methods of producing transgenic plants also are reviewed in Plant Biochemistry and Molecular Biology (eds. Lea and Leegood, John Wiley & Sons, 1993, pp. 275-295) and in Plant Biotechnology and Transgenic Plants (eds. Oksman-Caldentey and Barz, 2002).

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The fluorescent proteins of the present invention (as well as other components of the subject invention described herein) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In some embodiments relating to the method for labeling a biological molecule, cell or cell organelle, the subject proteins find use as labels (or reporter molecules) in cell and molecular biology assays. The assays of interest include but not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as a biomolecule labels, or cell organelle labels in living and fixed cells; as a markers in cell or organelle fusion, as a cell or organelle integrity markers, as a transfection markers (e.g. as labels for selection of transfected cells containing an expression vector encoding at least one fluorescent protein of the invention), as real-time probe working at near physiological concentrations, etc.

In particular, the subject proteins find use for identifying and/or measuring the expression of protein or polypeptide of interest in the biological material (e.g. host cells). This method comprises: i) introducing into a cell a nucleic acid molecule comprising a nucleotide sequence encoding a fluorescent protein according to the present invention wherein the nucleic acid molecule is operably linked to and under the control of an expression control sequence which moderates expression of the protein or polypeptide of interest; ii) culturing the cell under conditions suitable for the expression of the protein of interest; and iii) detecting the fluorescence emission of the fluorescent protein as a means of measuring the expression/localization of the protein of interest.

In particular, the subject proteins find use for identifying and/or localization of protein or polypeptide of interest in biological material. This method comprises: i) introducing into a cell a nucleic acid molecule comprising a nucleotide sequence encoding a fluorescent protein according to the present invention wherein the nucleic acid molecule is operably linked with sequence encoding protein or polypeptide of interest and under the control of an promoter sequence; ii) culturing the cell under conditions suitable for the expression of the protein of interest; and iii) detecting the fluorescence emission of the fluorescent protein as a means of measuring the expression/localization of the protein of interest.

The term "operatively linked" or "operably linked" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein of the present invention can be fused to a fusion partner of interest. In this case, the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention.

The applications of interest include the use of the subject proteins in fluorescence resonance energy transfer (FRET) methods. In these methods, the subject proteins serve as fluorescence acceptors in combination with a second fluorescent protein or dye, for example, a fluorescent protein as described in Matz et al., Nature Biotechnology 17:969-973 (1999); green fluorescent protein from *Aequorea Victoria* and mutants thereof, for example, as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; cyanine dyes such as Cy3 and Cy5; macrocyclic chelates of lenthaninde ions, such as quantum dye; and chemilumescent dyes such as luciferases, including those described in U.S. Pat. Nos. 5,843,746; 5,700, 673; 5,674,713; 5,618,722; 5,418,155; 5,330,906; 5,229,285; 5,221,623; 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has Ca2+ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528;

5,707,804; 5,688,648; 5,439,797; the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins find also use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the fluorescent protein by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescent activity, because parts of the functional chromophore are divided by the spacer. The spacer is framed by two identical protease-specific cleavage sites. Upon cleavage via the activated protease, the spacer would be cut out and the two residual "subunits" of the fluorescent protein would be able to reassemble to generate a functional fluorescent protein. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject fluorescent proteins also find use as biosensors in prokaryotic and eukaryotic cells, such as a $Ca^{2+}$ ion indicator; a pH indicator; a phosphorylation indicator; or as an indicator of other ions, such as magnesium, sodium, potassium, chloride and halides. Methods of using fluorescent proteins as biosensors also include those described in U.S. Pat. Nos. 5,972,638; 5,824,485 and 5,650,135 (as well as the references cited therein) the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. Kits typically include the protein of the invention as such, or a nucleic acid encoding the same preferably with the elements for expressing the subject proteins, for example, a construct such as a vector comprising a nucleic acid encoding the subject protein. In preferred embodiments kits may be used for monitoring pH within living cells, subcellular structures or protein around. In other embodiments kits may be used for labeling of cells, subcellular structures or proteins.

The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following example is offered by way of illustration and not by way of limitation.

EXAMPLES

Site directed mutagenesis and C-terminus replacement were performed by overlap-extension PCR (Ho, et al., 1989; *Gene* 77, 51-59), with primers containing the appropriate target substitutions. Clontech Diversity PCR Random Mutagenesis kit was used for random mutagenesis, in conditions optimal for 7 mutations per 1000 bp. For bacterial expression, a PCR-amplified BamHI/HindIII fragment encoding a fluorescent protein variant was cloned into the pQE30 vector (Qiagen). For expression in eukaryotic cells, a PCR-amplified AgeI/NotI fragment encoding a fluorescent protein variant was swapped for TurboGFP within the pTurboGFP-N vector (Evrogen).

Example 1

Generation of the Katushka-9-5

Commercially available nucleic acid encoding Katushka (TurboFP635) protein (SEQ ID NOs:1) was obtained (Evrogen JSC Russia). Site directed mutagenesis of Katushka was performed to obtain Katushka-9-5 variant comprising R201K substitution resulting in reduced protein aggregation in vitro as compared with Katushka. Mutation V6E that makes Katushka closer to the wild type protein eqFP578 (Merzlyak et al., 2007) was also introduced. Mutant variant obtained was transformed in *E. coli* (XL1-blue strain). *E. coli* colonies expressing mutant proteins were grown at 37 degree C. and recombinant proteins were purified via a metal-affinity resin TALON (Clontech). Purified proteins were tested for aggregation in vitro. For this, protein samples with concentration above 10 mg/ml were incubated for 48 hours at 4 degree C. Katushka forms visible aggregates in these conditions. Katushka-9-5 does not form visible aggregates in identical conditions. Sequencing of the Katushka-9-5 nucleic acid showed that the protein also comprises T9S substitution as compared to Katushka.

Excitation and emission spectra of Katushka-9-5 were analyzed using Varian Cary Eclipse Fluorescence Spectrophotometer. The spectra were similar to that of the initial Katushka protein with excitation/emission maxima at 588/635 nm, respectively.

To compare cytotoxicity of Katushka-9-5 and Katushka in vivo, we have exploited plasmid microinjection in the animal poles of *Xenopus laevis* embryos at 2-cells stage (20 pg/blastomere), tracking the death rate by the tailbud stage (stage 25) and by the tadpole stage (stage 42). Altogether, 600 embryos were microinjected in 5 independent experiments, which demonstrated significantly lower toxicity of Katushka-9-5 comparing with Katushka (FIG. 1).

Example 2

Generation of Kat650-21, the Far-Red Shifted Mutant of Katushka-9-5

A nucleic acid encoding Katushka-9-5 protein (SEQ ID NOs:7, 8) was obtained as described in the Example 1 and subjected to saturated site-directed mutagenesis (all 20 amino acid variants) at amino acid position M44 and overall random mutagenesis. Resulting library of mutant variants was transformed in *E. coli* (XL1-blue strain). Approximately 100,000 *E. coli* colonies expressing mutant protein variants were grown at 37 degree C. overnight and screened for the bright far-red shifted fluorescent variants using fluorescent stereomicroscope equipped with appropriate filter sets and built-in fluorescent spectrophotometer. The bright far-red shifted mutant variant was selected, named Kat650-21 (SEQ ID NOs: 9, 10). As compared to Katushka-9-5, Kat650-21 comprises site directed amino acid substitution M44A that provides far-red shift, and random amino acid substitution D24G, that presumably enhances protein folding. Kat650-21 is characterized by bright far-red fluorescence with excitation/emission peaked at 588/650 nm.

Example 3

Generation of Kat670-23, the Far-Red Shifted Mutant of Kat650-21

A nucleic acid encoding Kat650-21 was obtained as described in the Example 2 and subjected to saturated site-directed mutagenesis (all 20 amino acid variants) at amino acid positions M14, M44, S146, S161. Approximately 100,000 *E. coli* colonies expressing mutant protein variants were grown at 37 degree C. overnight and screened for the bright far-red shifted fluorescent variants using fluorescent stereomicroscope equipped with appropriate filter sets and built-in fluorescent spectrophotometer. The most far-red shifter variant was selected, named Kat670-23 (SEQ ID NOs: 11, 12). As compared to Katushka-9-5, Kat670-23 contains amino acid substitutions D24G, M14T, M44C, S146N, and S161N.

Kat670-23 is characterized by far-red fluorescence with excitation/emission peaked at 602/668 nm.

Example 4

Site-Directed Mutagenesis of Kat670-23

A nucleic acid encoding Kat670-23 was obtained as described in the Example 3 and subjected to saturated site-directed mutagenesis (all 20 amino acid variants) at amino acid position L16. Approximately 1,000 E. coli colonies expressing mutant protein variants were grown at 37 degree C. overnight and screened for the far-red shifted fluorescent variants using fluorescent stereomicroscope equipped with appropriate filter sets and built-in fluorescent spectrophotometer. The most far-red shifter variants were selected, named Kat683-1 (SEQ ID NOs: 19, 20) and KatX1 (SEQ ID NOs; 13, 14). As compared to Katushka-9-5, Kat683-1 comprises amino acid substitutions D24G (folding), M14T (far-red shift), L16N (far-red shift), M44C (far-red shift), S146N (far-red shift), and S161N (far-red shift). Kat683-1 is characterized by far-red fluorescence with excitation/emission peaked at 607/683 nm. KatX1 comprises amino acid substitutions M14T (far-red shift), L16E (far-red shift), D24G (folding), M44C (far-red shift), S146N (far-red shift), and S161N (far-red shift).

Example 5

Site-Directed Mutagenesis of Kat650-21

A nucleic acid encoding Kat650-21 (SEQ ID NOs: 9, 10) was obtained as described in the Example 2 and subjected to saturated site-directed mutagenesis (all 20 amino acid variants) at amino acid positions M14 and L16. Resulting library of mutant variants was transformed in E. coli (XL1-blue strain). Approximately 10,000 E. coli colonies expressing mutant protein variants were grown at 37 degree C. overnight and screened for the far-red fluorescent variants using fluorescent stereomicroscope and built-in fluorescent spectrophotometer. The bright far-red variant, KatX2 (SEQ ID NOs; 15, 16), was selected and sequenced. As compared with Katushka-9-5, KatX2 carries substitutions M14S (far-red shift), L16E (far-red shift), D24G (folding), and M44A (far-red shift).

Example 6

Generation of Katushka 9-5A, the Enhanced Mutant of Katushka-9-5

A nucleic acid encoding Katushka-9-5 protein (SEQ ID NOs:7, 8) was obtained as described in the Example 1 and subjected to site-directed mutagenesis S161A. Resulting mutant variant, named Katushka 9-5A (SEQ ID NOs: 19, 20), was characterized by enhanced brightness and maturation rate. Katushka 9-5A is characterized by bright far-red fluorescence with excitation/emission peaked at 588/633 nm.

Example 7

Characterization of Kat650-21 and Kat670-23

Nucleic acids encoding Kat650-21 and Kat670-23 proteins were obtained as described in the Examples 2 and 3, cloned into pQE30 vector (Qiagen) and transformed in E. coli (XL1-blue strain). E. coli colonies expressing mutant proteins were grown at 37 degree C. and recombinant proteins were purified via a metal-affinity resin TALON (Clontech). Purified proteins were used to obtain main spectral and biochemical characteristics.

Figure 3:
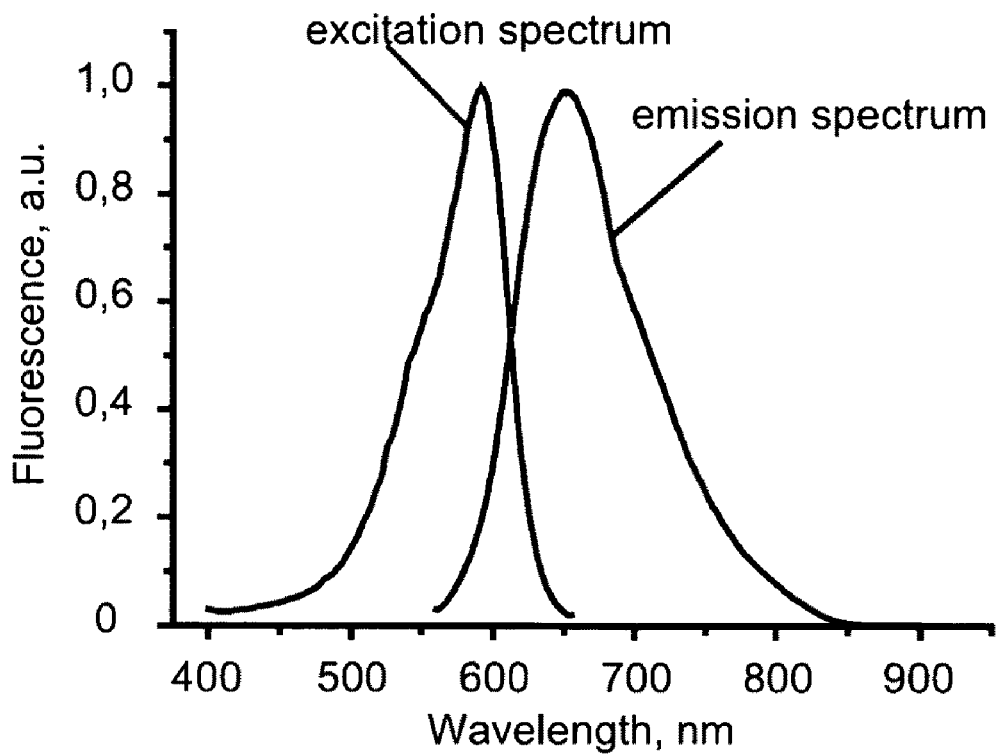
FIG. 3 illustrates normalized excitation and emission spectra of the Kat650-21 fluorescent protein.
Figure 4:
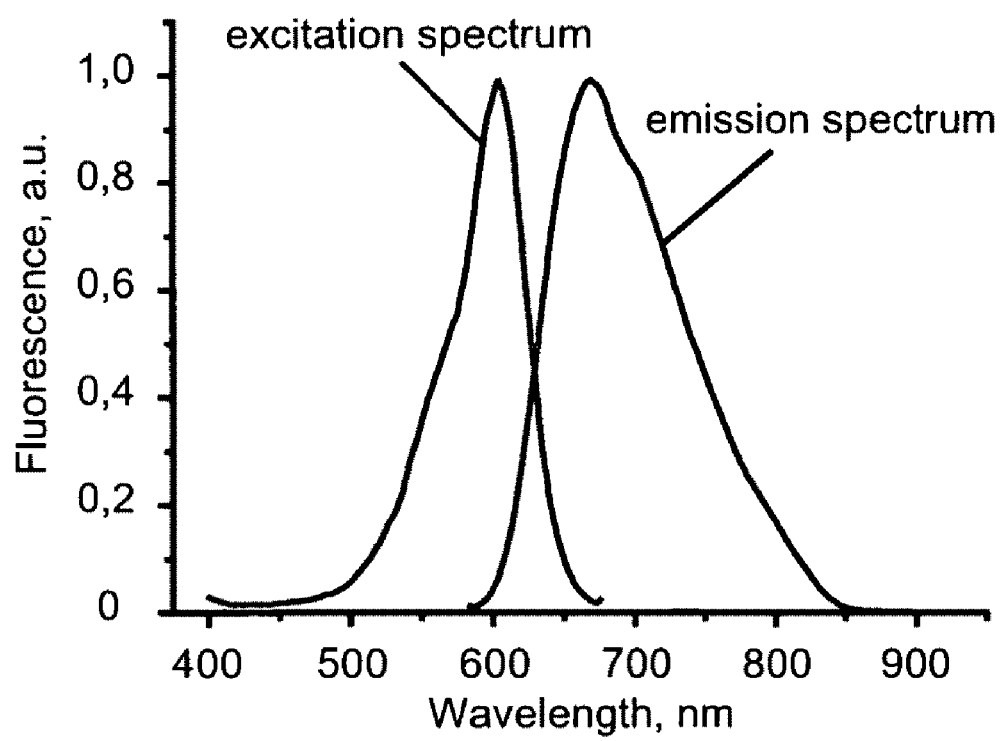
FIG. 4 illustrates normalized excitation and emission spectra of the Kat670-23 fluorescent protein.

Spectral characteristics of the purified proteins were obtained using Varian Cary Eclipse Fluorescence Spectrophotometer. FIGS. 3 and 4 illustrate corrected excitation and emission spectra of the Kat650-21 and Kat670-23 proteins.

pH titrations was performed by using a series of buffers in the pH range from 3 to 10. For each pH value, an aliquot of purified protein was diluted in an equal volume of the corresponding buffer solution and the fluorescence brightness was measured after 1 h incubation at room temperature. For accuracy, the actual pH was measured in each sample using a microelectrode (Sartorius).

Photostability comparison of Kat650-21 and Kat670-23 proteins with mNeptune (SEQ ID NO:4) and E2-Crimson (SEQ ID NO:26) far-red fluorescent proteins was performed. Nucleic acids encoding mNeptune (SEQ ID NO:3) and E2-Crimson (SEQ ID NO:25) were synthetically produced, cloned into pQE30 vector (Qiagen) and transformed in E. coli (XL1-blue strain). E. coli colonies were grown at 37 degree C. and recombinant proteins were purified via a metal-affinity resin TALON (Clontech).

Figure 5:
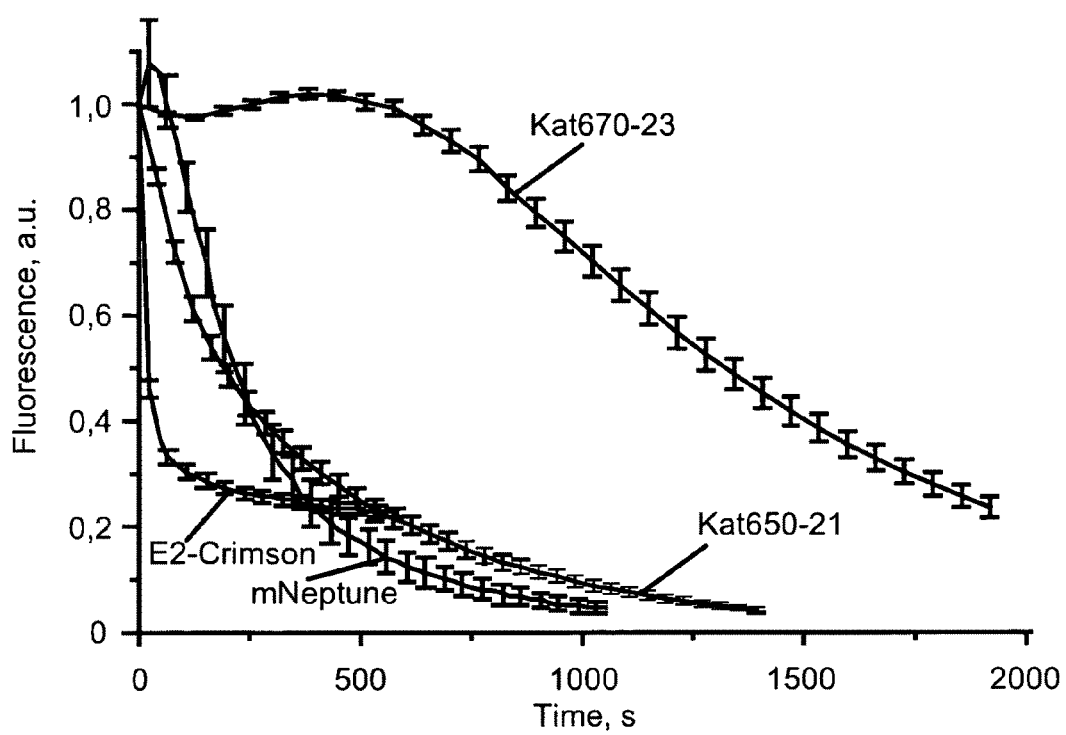
FIG. 5 illustrates normalized photobleaching curves for Kat650-21, Kat670-23, mNeptune and E2-Crimson using widefield fluorescence microscopy under metal halide illumination. Standard deviations (n=4 experiments) are shown.
Figure 6:
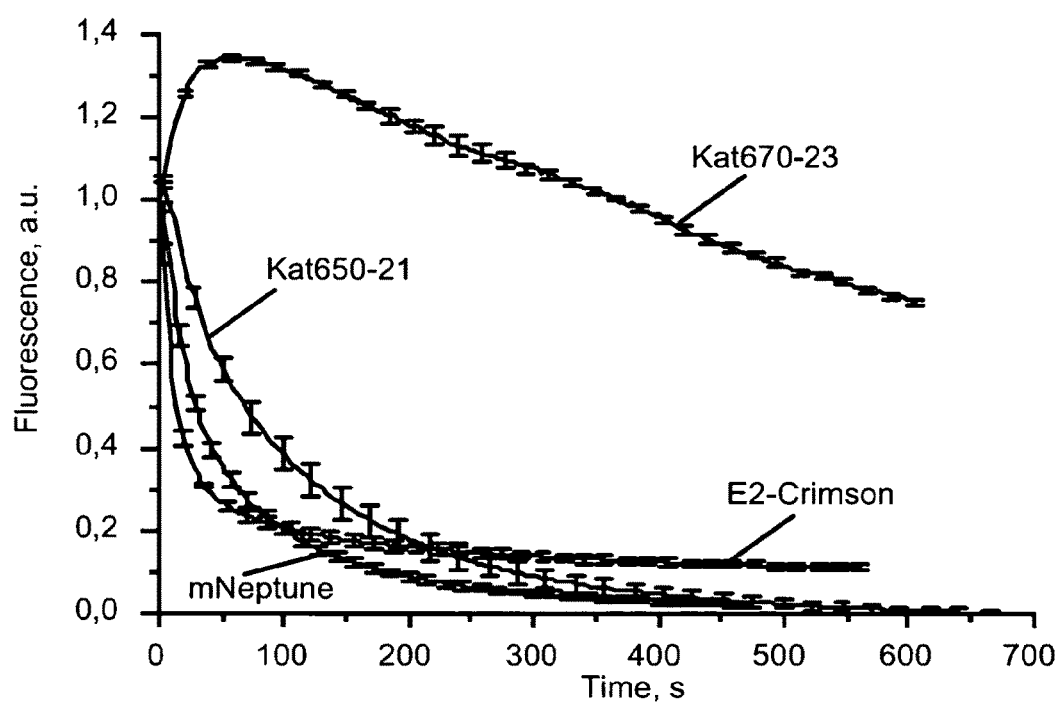
FIG. 6 illustrates normalized photobleaching curves for Kat650-21, Kat670-23, mNeptune and E2-Crimson using laser scanning confocal microscopy. Standard deviations (n=4 experiments) are shown.

Selected proteins underwent photostability comparison test in LSM 510 Confocal Scanning Microscope from Carl Zeiss and epifluorescent Leica AFLX 6000 microscopes. Proteins carrying 6×His tags were bound to Talon metal affinity resin beads, placed onto a glass slide and exposed to the light. While bleaching by a 561 nm laser line in confocal microscope the following parameters were used: 63× oil immersion objective, zoom 1.5×, scan rate: 4 s per image, maximal power. While bleaching by mercury arc lamp the TexasRed filter set was used passing 546 nm peak of mercury lamp. Bleaching times were corrected on the molar extinction coefficients of the corresponding fluorescent protein at 546 or 561 nm. Kat670-23 demonstrated extremely high photostability both in widefield (FIG. 5) and confocal (FIG. 6) microscopy, which is remarkable for FPs and should allow for accumulation of the fluorescent signal over long exposure times. It should be noted that the combination of amino acid residues 148N and 165N in Kat670-23 is unique and has never been encountered in other FPs. This implies rather tight packing around the chromophore, which probably forms the basis of the high photostability and pH resistance of the FP.

Characteristics of Kat650-21 and Kat670-23 are summarized in Table 1.

To compare efficiency of infrared imaging of FPs, we have employed imaging system Biospec (Moscow, Russia). The excitation at 635 nm with photodiodes was used and emission was measured over the integrated 700-900 nm range. To compare infrared signal of FPs in living tissues, we performed subcutaneous (2-mm depth) and intramuscular (5-mm depth) injections of equal portions of Katushka, Kat650-21 or Kat670-23 protein samples into living mice. In this system, Kat670-23 exhibited the highest infrared signal, both in subcutaneous and intramuscular injection experiments.

Example 8

Expression of Kat650-21 and Kat670-23 in Mammalian Cells

Nucleic acids encoding Kat650-21 and Kat670-23 were obtained as described in the Examples 2 and 3, respectively, and operatively cloned into the pTurboGFP-N vector (Evrogen) in place of TurboGFP sequence under the control of CMV promoter. HeLa cells transiently transfected with these constructs became brightly fluorescent after 16 h and 18 h of incubation at 37 degree C., for Kat650-21 and Kat670-23, respectively.

TABLE 1

Key characteristics of Kat650-21 and Kat670-23 in comparison with other far-red fluorescent proteins. QY, quantum yield; EC, molar extinction coefficient; IR, infrared. Brightness is calculated as the product of the molar extinction coefficient and quantum yield. Brightness in IR is calculated as the product of the extinction coefficient at 635 nm, quantum yield and emission fraction between 700 and 900 nm. Photostability is measured as half-time of photobleaching (sec).

|  | mCherry | Katushka2 | Katushka | RFP639 | E2-Crimson | mPlum | mNeptune | Kat650-21 | Kat670-23 |
|---|---|---|---|---|---|---|---|---|---|
| Excitation peak, nm | 587 | 588 | 588 | 588 | 605 | 590 | 599 | 592 | 605 |
| Emission peak, nm | 610 | 633 | 635 | 639 | 646 | 649 | 649 | 650 | 670 |
| Fluorescence QY | 0.22 | 0.37 | 0.34 | 0.18 | 0.12 | 0.10 | 0.18 | 0.24 | 0.06 |
| EC, $M^{-1} cm^{-1}$, at excitation maximum | 72,000 | 69,000 | 65,000 | 69,000 | 58,500 | 41,000 | 57,500 | 65,000 | 70,000 |
| Brightness | 15,840 | 25,530 | 22,100 | 12,420 | 7,080 | 4,100 | 10,350 | 15,600 | 4,200 |
| EC, at 635 nm | 1,000 | 1,600 | 1,700 | 2,000 | 12,640 | 1,000 | 7,900 | 4,300 | 15,700 |
| QY in IR (700-900 nm) | 0.04 | 0.07 | 0.07 | 0.05 | 0.03 | 0.03 | 0.05 | 0.07 | 0.03 |
| Brightness in IR | 40 | 112 | 119 | 100 | 379 | 30 | 395 | 301 | 471 |
| Photostability, widefield | 601 | ND | ND | ND | 19 | ND | 216 | 190 | 1289 |
| Photostability, confocal | 48 | ND | 77 | ND | 14 | ND | 29 | 67 | >700 |
| pKa | 4.5 | 5.0 | 5.5 | ND | ND | <4.5 | 5.8 | 5.7 | 4.5 |
| Reference | Shaner et al., Nat Biotechnol (2004) 22 (12), 1567 | Shcherbo et al., Biochem J (2009) 418(3): 567-74 | Shcherbo et al., Nat Methods (2007) 4 (9), 741 | Kredel et al., Chem Biol (2008) 15 (3), 224 | Strack et al., Nat Methods (2008) 5 (11), 955 | Wang et al., PNAS (2004) 101 (48), 16745 | Lin et al., Chem Biol (2009) 16 (11), 1169 | — | — |

While the foregoing is directed to embodiments of the invention, other and further embodiments of the invention may be devised without departing from the basic scope thereof.

---

The invention claimed is:

1. A nucleic acid present in other than its natural environment, wherein the nucleic acid encodes a fluorescent protein that comprises a GFP-like domain, emits far-red fluorescence and has reduced tendency to aggregate relative to SEQ ID NO:2, wherein the protein comprises at least one substitution R201K as compared with SEQ ID NO:2.

2. The nucleic acid according to claim 1, wherein the GFP-like domain has a sequence identity of 90% or more to the GFP-like domain corresponding to residues 7-226 of amino acid sequence selected from the group consisting of SEQ ID NO: 8, 10, 12, 14, 16, 18, and 20.

3. The nucleic acid according to claim 1, wherein the protein has a sequence identity of 90% or more to full length protein selected from the group consisting of SEQ ID NO: 8, 10, 12, 14, 16, 18, and 20.

4. The nucleic acid according to claim 1, wherein the protein emits far-red shifted fluorescence relative to SEQ ID NO:2, wherein the protein comprises at least one substitution at a position corresponding to a position in SEQ ID NO:2 selected from the group consisting of position 14, 16, 44, 63, 146, 161, 163, 200, or 202.

5. The nucleic acid according to claim 4, wherein the GFP-like domain has a sequence identity of 90% or more to the GFP-like domain corresponding to residues 7-226 of amino acid sequence selected from the group consisting of SEQ ID NO: 8, 10, 12, 14, 16, 18, and 20.

6. The nucleic acid according to claim 4, wherein the protein has a sequence identity of 90% or more to full length protein selected from the group consisting of SEQ ID NO: 8, 10, 12, 14, 16, 18, and 20.

7. The nucleic acid according to claim 1, wherein the protein has the amino acid sequence of SEQ ID NOS: 8, 10, 12, 14, 16, 18, and 20.

8. A vector comprising the nucleic acid of claim 1.

9. An expression cassette comprising:
(a) the nucleic acid according to claim 1; and
(b) a transcriptional initiation region that is operatively linked to the nucleic acid in (a) and is functional in an expression host; and
(c) a transcriptional termination region that is operatively connected to the nucleic acid in (a) and is functional in the expression host.

10. A host cell or progeny thereof, comprising the expression cassette according to claim 9 as part of an extrachromosomal element or integrated into the genome of a host cell as a result of introduction of the expression cassette into the host cell.

11. A transgenic cell, or progeny thereof, comprising the nucleic acid according to claim 1.

12. A kit comprising at least one nucleic acid according to claim 1.

* * * * *

UNITED STATES PATENT AND TRADEMARK OFFICE
CERTIFICATE OF CORRECTION

PATENT NO. : 7,972,834 B2  
APPLICATION NO. : 12/803202  
DATED : July 5, 2011  
INVENTOR(S) : Lukyanov et al.

Page 1 of 1

It is certified that error appears in the above-identified patent and that said Letters Patent is hereby corrected as shown below:

In the Summary of the Invention:

Column 4, Line 52, please delete "M145" and insert --M14S-- therefor;

In the Detailed Description:

Column 16, Line 25, please delete "M145" and insert --M14S-- therefor.

Signed and Sealed this  
Fourth Day of October, 2011

David J. Kappos  
*Director of the United States Patent and Trademark Office*